(12) United States Patent
Tyber et al.

(10) Patent No.: US 9,877,752 B2
(45) Date of Patent: Jan. 30, 2018

(54) INTRAOSSEOUS INTRAMEDULLARY FIXATION ASSEMBLY AND METHOD OF USE

(71) Applicant: Extremity Medical LLC, Parsippany, NJ (US)

(72) Inventors: Jeff Tyber, Bethlehem, PA (US); Jamy Gannoe, West Milford, NJ (US); Lawrence Kiefer, Lafayette, NJ (US)

(73) Assignee: Extremity Medical LLC, Parsippany, NJ (US)

( * ) Notice: Subject to any disclaimer, the term of this patent is extended or adjusted under 35 U.S.C. 154(b) by 0 days.

(21) Appl. No.: 15/181,435

(22) Filed: Jun. 14, 2016

(65) Prior Publication Data

US 2016/0278823 A1   Sep. 29, 2016

Related U.S. Application Data

(60) Continuation of application No. 14/599,671, filed on Jan. 19, 2015, now Pat. No. 9,364,271, which is a division of application No. 12/658,680, filed on Feb. 11, 2010, now Pat. No. 9,044,282, which is a continuation-in-part of application No. 12/456,808, filed on Jun. 23, 2009, now Pat. No. 8,303,589.

(60) Provisional application No. 61/132,932, filed on Jun. 24, 2008.

(51) Int. Cl.
| | |
|---|---|
| *A61B 17/56* | (2006.01) |
| *A61B 17/72* | (2006.01) |
| *A61B 17/17* | (2006.01) |
| *A61B 17/86* | (2006.01) |
| *A61F 2/42* | (2006.01) |

(52) U.S. Cl.
CPC ...... *A61B 17/7291* (2013.01); *A61B 17/1717* (2013.01); *A61B 17/1775* (2016.11); *A61B 17/72* (2013.01); *A61B 17/8605* (2013.01); *A61B 17/8625* (2013.01); *A61B 17/1782* (2016.11); *A61B 2017/564* (2013.01); *A61F 2002/4238* (2013.01); *Y10S 411/954* (2013.01)

(58) Field of Classification Search
CPC ............. A61B 17/7291; A61B 17/8605; Y10S 411/912; Y10S 411/954
USPC .................................................. 411/271, 174
See application file for complete search history.

(56) References Cited

U.S. PATENT DOCUMENTS

| | | | | |
|---|---|---|---|---|
| 5,984,681 A | * | 11/1999 | Huang | .................... A61C 8/001 433/173 |
| 6,261,039 B1 | * | 7/2001 | Reed | ......................... B23P 6/04 411/178 |
| 6,517,541 B1 | * | 2/2003 | Sesic | ..................... A61B 17/72 606/62 |

(Continued)

*Primary Examiner* — Ellen C Hammond
*Assistant Examiner* — Stuart S Bray
(74) *Attorney, Agent, or Firm* — Kelley Drye & Warren LLP

(57) ABSTRACT

An intramedullary assembly for intraosseous bone fusion includes a lag screw member and a tapered screw member. The lag screw member includes a first elongated body, where the first elongated body includes a first threaded portion at a first end and a bulbous portion at a second end. The tapered screw member is coupled to the lag screw member, and the tapered screw member includes a second elongated body, where the second elongated body includes a second threaded portion at a third end, and an opening at a fourth end.

21 Claims, 20 Drawing Sheets

(56) References Cited

U.S. PATENT DOCUMENTS

| | | | | |
|---|---|---|---|---|
| 6,629,976 B1* | 10/2003 | Gnos | A61B 17/7291 | 606/62 |
| 6,908,271 B2* | 6/2005 | Breslin | F16B 13/126 | 411/271 |
| 7,033,365 B2* | 4/2006 | Powell | A61B 17/921 | 606/104 |
| 7,524,326 B2* | 4/2009 | Dierks | A61B 17/7041 | 606/308 |
| 7,608,097 B2* | 10/2009 | Kyle | A61B 17/7098 | 606/304 |
| 7,909,825 B2* | 3/2011 | Saravia | A61B 17/1725 | 606/63 |
| 7,938,848 B2* | 5/2011 | Sweeney | A61B 17/1671 | 606/246 |
| 7,951,171 B2* | 5/2011 | Woods | A61B 17/7032 | 606/264 |
| 8,114,141 B2* | 2/2012 | Appenzeller | A61B 17/68 | 606/306 |
| 2002/0128712 A1* | 9/2002 | Michelson | A61F 2/446 | 623/17.11 |
| 2004/0006345 A1* | 1/2004 | Vlahos | A61B 17/8625 | 606/916 |
| 2005/0107791 A1* | 5/2005 | Manderson | A61B 17/68 | 606/62 |
| 2005/0277940 A1* | 12/2005 | Neff | A61B 17/7225 | 606/916 |
| 2006/0173461 A1* | 8/2006 | Kay | A61B 17/8625 | 606/304 |
| 2006/0189991 A1* | 8/2006 | Bickley | A61B 17/864 | 606/916 |
| 2006/0264954 A1* | 11/2006 | Sweeney, II | A61B 17/8685 | 606/312 |
| 2007/0162028 A1* | 7/2007 | Jackson | A61B 17/8635 | 606/86 A |
| 2009/0093851 A1* | 4/2009 | Osman | A61B 17/7064 | 606/301 |
| 2009/0198289 A1* | 8/2009 | Manderson | A61B 17/864 | 606/304 |
| 2009/0281580 A1* | 11/2009 | Emannuel | A61B 17/8625 | 606/304 |
| 2010/0042164 A1* | 2/2010 | Lee | A61B 17/686 | 606/304 |
| 2010/0076499 A1* | 3/2010 | McNamara | A61B 17/0401 | 606/304 |
| 2010/0145397 A1* | 6/2010 | Overes | A61B 17/68 | 606/319 |
| 2010/0274296 A1* | 10/2010 | Appenzeller | A61B 17/8605 | 606/305 |
| 2011/0004255 A1* | 1/2011 | Weiner | A61B 17/1682 | 606/301 |
| 2011/0022066 A1* | 1/2011 | Sevrain | A61B 17/86 | 606/151 |
| 2011/0106177 A1* | 5/2011 | Lewis | A61B 17/686 | 606/305 |
| 2011/0184470 A1* | 7/2011 | Gorek | A61B 17/7011 | 606/279 |
| 2011/0282398 A1* | 11/2011 | Overes | A61B 17/861 | 606/304 |
| 2012/0022603 A1* | 1/2012 | Kirschman | A61B 17/7064 | 606/305 |

* cited by examiner

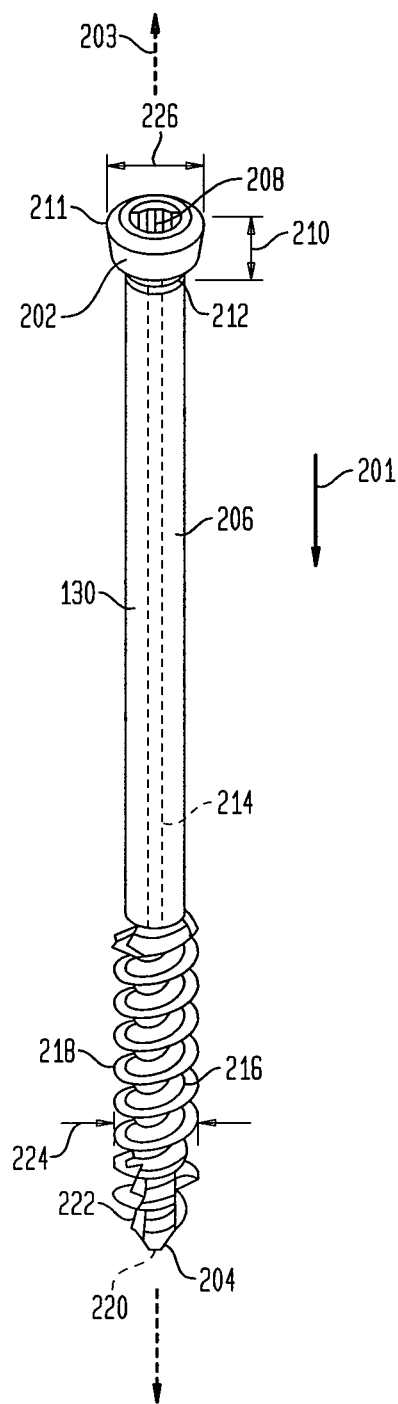

INTRAOSSEOUS INTRAMEDULLARY FIXATION ASSEMBLY AND METHOD OF USE

CROSS-REFERENCE TO RELATED APPLICATIONS

This application is a continuation of Non-Provisional application Ser. No. 14/599,671, filed on Jan. 19, 2015, which is a divisional of Non-Provisional application Ser. No. 12/658,680, filed Feb. 11, 2010, which is a continuation-in-part application of Non-Provisional application Ser. No. 12/456,808, filed Jun. 23, 2009, issued as U.S. Pat. No. 8,303,589 on Nov. 6, 2012, which claims the benefit of Provisional Application No. 61/132,932, filed Jun. 24, 2008, the entire contents of the entire chain of applications are herein incorporated by reference.

FIELD OF THE INVENTION

This invention relates to the field of orthopedic implant devices, and more particularly, to an intramedullary fixation assembly used for fusion of the angled joints, bones and deformity correction, such as the hand and foot bones.

BACKGROUND OF THE INVENTION

Orthopedic implant devices, such as intramedullary nails, plates, rods and screws are often used to repair or reconstruct bones and joints affected by trauma, degeneration, deformity and disease, such as Charcot arthropathy caused by diabetes in some patients, Hallux Valgus deformities, failed Keller Bunionectomies, Rheumatoid Arthritis, and severe deformities.

Moreover, infections and wound complications are a major concern in the aforementioned procedures. Wound closure is technically demanding for the surgeon, and devices that add surface prominence, such as plates or exposed screws, add to the difficulty by requiring greater tissue tension during incision reapproximation. This increases the risk of postoperative wound infections and dehiscence that may ultimately result in limb amputation.

Various implants have been utilized for surgical treatment of these bones and joints, including bone screws. Implants have also been utilized to treat severe deformities in the metatarsal and phalangeal bones, including multiple screws and plates. These multiple screws and plate implants have been commonly used in a first metatarsal-phalangeal fusion procedure to fuse the first metatarsal to the first phalangeal bone in hallux valgus deformities, failed keller bunionectomies, rheumatoid arthritis, and other types of severe deformities in the metatarsal and phalange bones. While these devices allow fixation and promote fusion, they do not deliver restoration of the arch in a Charcot foot, they are not effective in metatarsal-phalangeal (MTP) fusion procedures, nor do they deliver uniform compression for various predetermined angles of compression.

Particularly, screw implants in MTP procedures are ineffective in delivering sufficient compression to the bones in the foot, preventing screw head break out, or delivering effective bending resistance. Moreover, hard to control dorsiflexion and valgus angles as well skin irritation from proximity to the skin prevents these screw implants from being readily utilized for surgical treatment. Yet further, plate implants used with bone screws too have the same drawbacks as fixed varus and valgus angles, lack of direct compression across the MTP joint, and skin irritations from proximity to the skin reduce the effectiveness of these implants.

There is therefore a need for an intramedullary fixation assembly and method of use that overcomes some or all of the previously delineated drawbacks of prior fixation assemblies.

SUMMARY OF THE INVENTION

An object of the invention is to overcome the drawbacks of previous inventions.

Another object of the invention is to provide a novel and useful intramedullary fixation assembly that may be utilized to treat bones in a human body.

Another object of the invention is to provide a system for compressing bones using an intramedullary fixation assembly.

Another object of the invention is to fuse the bones in the human body through the use of an intraosseous intramedullary assembly.

Another object of the invention is to provide a fixed acute angle intramedullary fixation assembly for bone fixation.

Another object of the invention is to provide variable acute angles an intramedullary fixation assembly for bone fixation having variable acute angles of fixation.

Another object of the invention is to provide at least three point of compression on bone fragments through a variable angle intramedullary fixation assembly.

In a first non-limiting aspect of the invention, an intramedullary assembly for bone fusion is provided and includes a lag screw member and a tapered screw member. The lag screw member includes a first elongated body, where the first elongated body includes a first threaded portion at a first end and a bulbous portion at a second end. The tapered screw member is coupled to the lag screw member, and the tapered screw member includes a second elongated body, where the second elongated body includes a second threaded portion at a third end, and an opening at a fourth end.

In a second non-limiting aspect of the invention, a method for bone fusion includes eight steps. In step one, an intramedullary assembly is provided, where the intramedullary assembly includes a lag screw member having a first elongated body. The first elongated body includes a first threaded portion at a first end and a bulbous portion at a second end. The intramedullary assembly also includes a tapered screw member coupled to the lag screw member, where the tapered screw member includes a second elongated body having a second threaded portion at a third end, a tubular portion at a fourth end, and an opening at the fourth end. Step two includes making an incision in the foot. Step three includes drilling a first medullary canal in a first bone. Step four includes inserting the tapered screw member into the first medullary canal. Step five includes aligning the tapered screw member in the first medullary canal. Step six includes drilling a second medullary canal in the first bone. Step seven includes slideably coupling the lag screw member to the tapered screw member. Step seven includes inserting the lag screw member into the second medullary canal. Step eight includes applying compression to the lag screw member to lock the tapered screw member to the lag screw member, thereby fusing the first bone to the second bone.

BRIEF DESCRIPTION OF THE DRAWINGS

A further understanding of the invention can be obtained by reference to a preferred embodiment set forth in the illustrations of the accompanying drawings. Although the illustrated embodiment is merely exemplary of systems and methods for carrying out the invention, both the organization and method of operation of the invention, in general, together with further objectives and advantages thereof, may be more easily understood by reference to the drawings and the following description. The drawings are not intended to limit the scope of this invention, which is set forth with particularity in the claims as appended or as subsequently amended, but merely to clarify and exemplify the invention.

For a more complete understanding of the invention, reference is now made to the following drawings in which:

FIG. 2 is a perspective view of a proximal screw member used in the fixation system shown in FIG. 1 according to the preferred embodiment of the invention.

DETAILED DESCRIPTION

The invention may be understood more readily by reference to the following detailed description of preferred embodiment of the invention. However, techniques, systems, and operating structures in accordance with the invention may be embodied in a wide variety of forms and modes, some of which may be quite different from those in the disclosed embodiment. Consequently, the specific structural and functional details disclosed herein are merely representative, yet in that regard, they are deemed to afford the best embodiment for purposes of disclosure and to provide a basis for the claims herein, which define the scope of the invention. It must be noted that, as used in the specification and the appended claims, the singular forms "a", "an", and "the" include plural referents unless the context clearly indicates otherwise.

Figure 1:
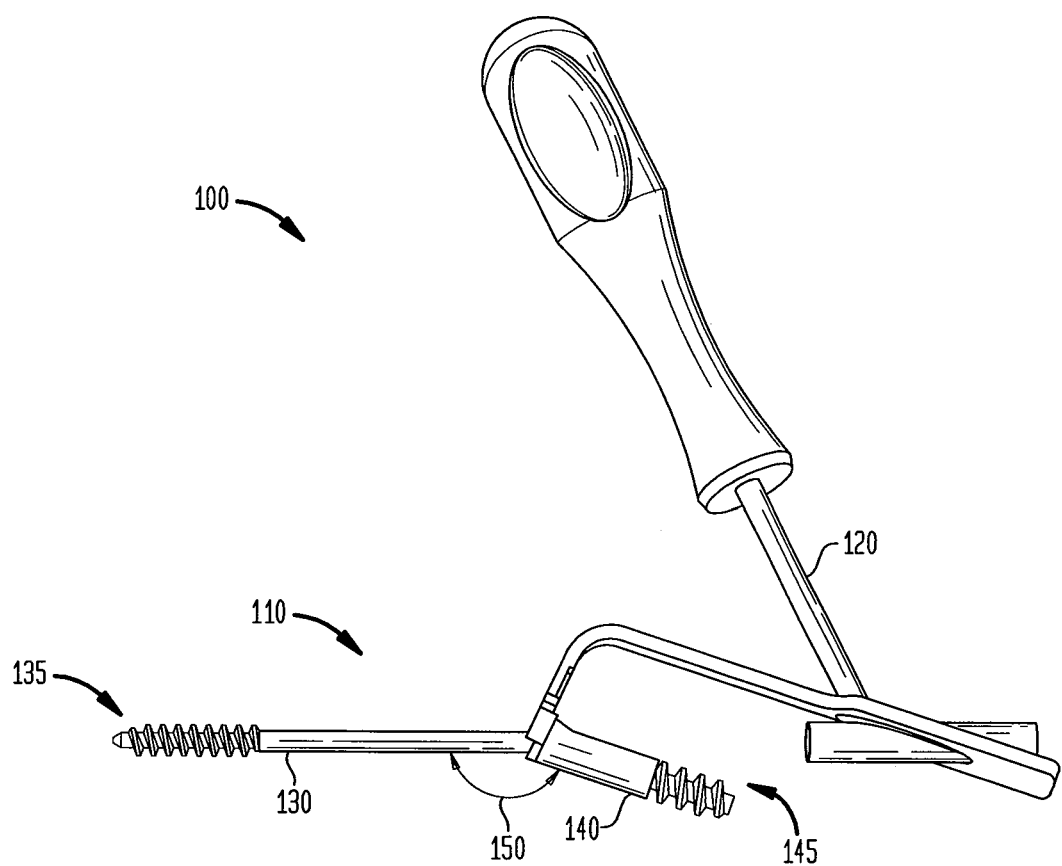
FIG. 1 is a perspective view of a fixation system according to a preferred embodiment of the invention.

Referring now to FIG. 1, there is shown a fixation system 100 which is made in accordance with the teachings of the preferred embodiment of the invention. As shown, the fixation system 100 includes an intramedullary fixation assembly 110, comprising a proximal screw member 130 and a distal member 140. Proximal screw member 130 is provided on proximal end 135 of assembly 110 and is coupled to a distal member 140 that is provided on the distal end 145 of the fixation assembly 110. Also, proximal screw member 130 makes a fixed angle 150 with distal member 140 and this angle 150 determines the angle for arch restoration. Moreover, fixation system 100 includes instrument 120 that is utilized to couple intramedullary fixation assembly 110 to the bones in the mid-foot region (not shown). It should be appreciated that in one non-limiting embodiment, intramedullary fixation assembly 110 may be made from a Titanium material, although, in other non-limiting embodiments, intramedullary fixation assembly 110 may be made from SST, PEEK, NiTi, Cobalt chrome or other similar types of materials.

As shown in FIG. 2, proximal screw member 130 is generally cylindrical in shape and extends from first bulbous portion 202 to second tapered end 204. End 204 has a diameter that is slightly smaller than diameter 226 of bulbous portion 202. Additionally, bulbous portion 202 has a taper, such as a Morse taper, with a width that decreases from end 211 to end 212. The taper allows for a locked interference fit with tapered aperture 316 when tapered bulbous portion 202 is combined with tapered aperture 316, shown and described below. Moreover, bulbous portion 202 is generally circular and has a generally hexagonal torque transmitting aperture 208 that traverses length 210 of bulbous portion 202. However, a star-shaped aperture, a square-shaped aperture, or any other shaped aperture may be utilized without departing from the scope of the invention. Torque transmitting aperture 208 is utilized to transmit a torque from bulbous portion 202 to tapered end 204 by rotating bulbous portion 202.

Further, proximal screw member 130 has a first smooth exterior portion 206 extending from end 212 of bulbous portion 202. Portion 206 comprises an internal aperture 214 that longitudinally traverses portion 206 in direction 201. Portion 206 terminates into a second generally tubular portion 216. Portion 216 may comprise internal circular aperture 220 that longitudinally traverses inside portion 216. Internal circular aperture 220 is aligned with apertures 214 and 208 along axis 203 to form a continuous opening (i.e., a cannula) from bulbous portion 202 to end 204. The continuous opening or cannula is provided to interact with a guide wire (not shown) by receiving the guide wire within the continuous opening thereby positioning and locating the proximal member 130. In other non-limiting embodiments, the proximal member 130 may be provided without apertures 220 and 214 (i.e., the proximal member is solid).

Furthermore, tubular portion 216 has a plurality of circular threads, such as threads 218, which are circumferentially disposed on the external surface of portion 216 and, with threads 218 having an external diameter 224. Portion 216 may also be provided with a self-tapping leading edge 222 to provide portion 216 with the ability to remove bone material during insertion of proximal screw member 130 into bone. It should be appreciated that the length of the proximal member 130 may be selected of varying lengths to allow a surgeon to fuse different joints in a foot (not shown).

Figure 3A:
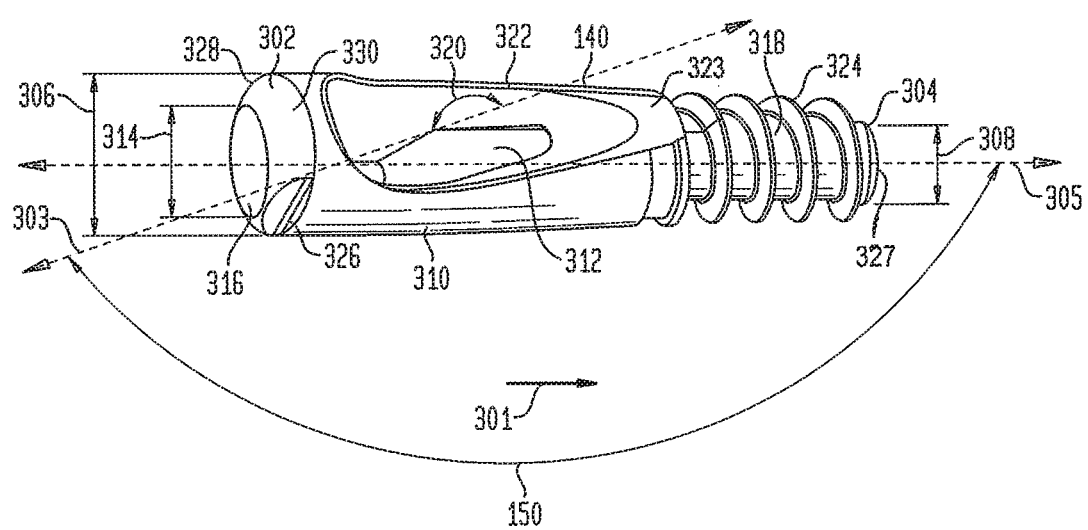
FIG. 3A is a perspective view of a distal member used in the fixation system shown in FIG. 1 according to the preferred embodiment of the invention.
Figure 3B:
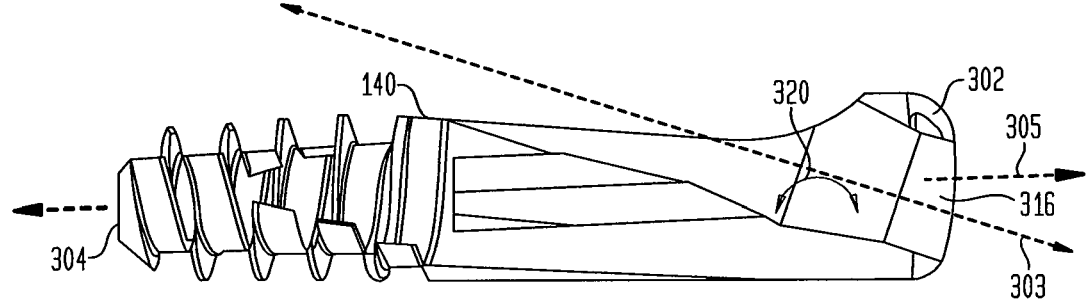
FIG. 3B is a perspective cross-sectional view of the distal member shown in FIG. 3A according to the preferred embodiment of the invention.

As shown in FIGS. 3A-3B, distal member 140 of the preferred embodiment is generally tubular in shape and tapers from a first end 302 to a second end 304 (i.e. end 302 has a diameter 306 that is slightly larger than diameter 308 of end 304). However, in another non-limiting embodiment, distal member 140 has a constant width from first end 302 to second end 304. Further, first end 302 is generally semi-spherical in shape and has an internal circular aperture 316, which traverses end 302 along direction 301 (i.e. end 302 is generally "donut" shaped). Additionally, circular aperture 316 emanates from surface 322, such that portion 310 has a generally tapered aperture 316 provided in portion 310. Circular aperture 316 comprises slope 320 from first end 302 to end 323 of portion 310. Further, aperture 316 is aligned along axis 303, which is offset from horizontal axis 305 of distal member 140. Axis 303 forms an angle 150 with horizontal axis 305 that determines the angle for arch restoration, as shown in FIG. 3A. Angle 150 may be any angle greater than 90 degrees and less than 180 degrees. Tapered aperture 316 when combined with tapered bulbous portion 202, shown in FIG. 2, creates a locked interference fit between proximal member 130 and distal member 140. First end 302 has a plurality of substantially similar grooves 326 and 328, which form an "L-shape" with surface 330 of end 302. Grooves 326 and 328 are provided to receive instrument 120 of fixation system 100, which is later described. In other non-limiting embodiments, other similar instruments may be provided to be received within grooves 326 and 328.

Distal member 140 further comprises a generally smooth portion 310 coupled to end 302. Portion 310 has a generally hexagonal shaped aperture 312, which opens into aperture 316 and which longitudinally traverses through portion 310 in direction 301. In other non-limiting embodiments, a star-shaped aperture, a square-shaped aperture, or any other shaped aperture may be utilized. Circular aperture 316 has a diameter 314 that is slightly larger than external diameter 224 of portion 216 and 206 of proximal screw member 130, with portions 216 and 206 being slidably received within aperture 316 of portion 310. Aperture 316 has a diameter that is smaller than diameter 226 of bulbous portion 202.

Portion 310 of distal member 140 terminates into a second generally cylindrical portion 318 which has a plurality of threads 324, which are circumferentially disposed on the external surface of portion 318. Portion 318 has an internal circular aperture 327 which is longitudinally coextensive with portion 318 in direction 301. Circular aperture 327 aligns with aperture 312 to form a continuous opening from end 302 to end 304.

Figure 4:
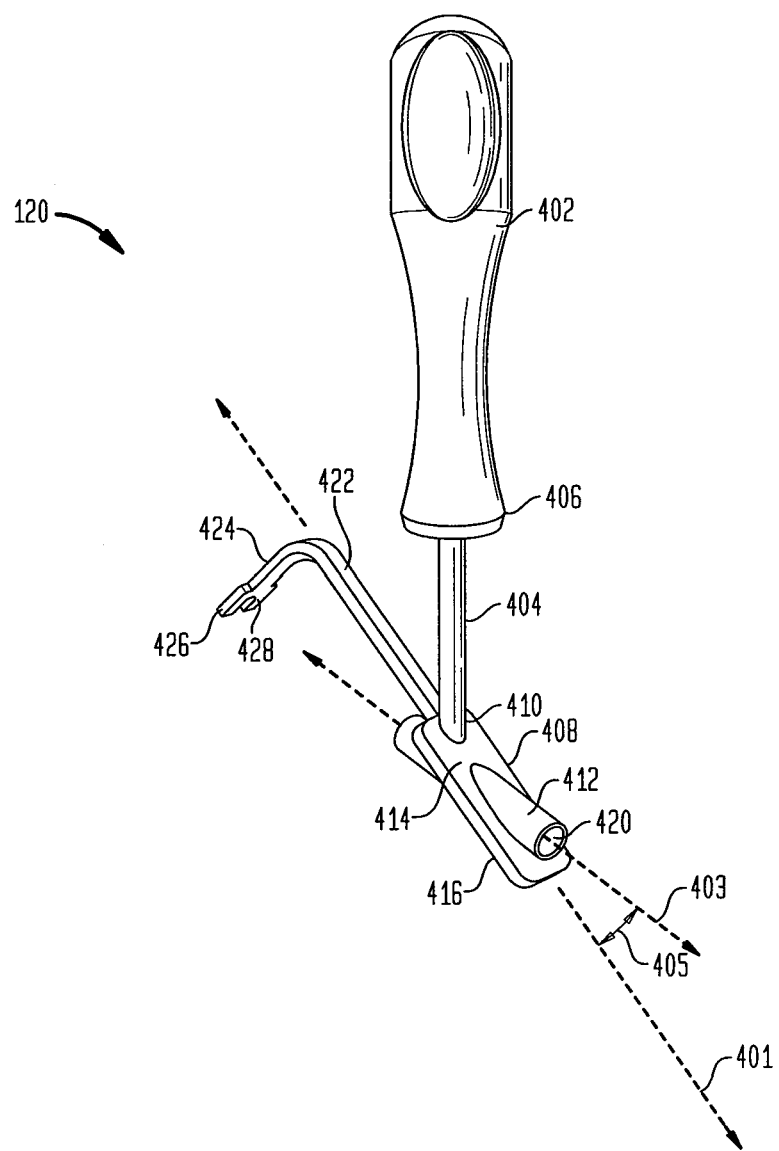
FIG. 4 is a perspective view of the instrument member used in the fixation system shown in FIG. 1 according to the preferred embodiment of the invention.

As shown in FIG. 4, instrument 120 is illustrated for coupling proximal screw member 130 to distal member 140. Particularly, instrument 120 includes a handle portion 402 coupled to a rod portion 404. Rod portion 404 emanates from handle portion 402 at end 406 and terminates into a rectangular planar portion 408 at end 410. Planar portion 408 is aligned along axis 401 and is fixably coupled to a generally cylindrical tubular portion 412 (i.e., an aiming device). Portion 412 traverses portion 408 from top surface 414 to bottom surface 416. Further, tubular portion 412 is aligned along dissimilar axis 403, forming an angle 405 with axis 401. Also, tubular portion 412 has a through aperture 420 that longitudinally traverses portion 412 along axis 403.

Planar portion 408 is coupled to planar portion 422, with portion 422 having a width slightly smaller than width of portion 408. Portion 422 terminates into a generally "U-shaped" portion 424 with portion 424 being orthogonal to portion 422. Further, portion 424 has a plurality of substantially similar sides 426 and 428 which are provided to be slidably coupled to grooves 326 and 328 of distal member 140.

In operation, sides 426 and 428 of instrument 120 are received in respective grooves 326 and 328 of distal member 140, of FIGS. 3A-3B, thereby slidably coupling distal member 140 to instrument 120. In this position, axis 303 of aperture 316 is aligned along substantially the same axis as axis 403 of instrument 120. Proximal screw member 130 is coupled to distal member 140 by slidably coupling portions 206 and 216 through aperture 420 of tubular portion 412. Tubular portion 412 guides proximal screw member 130 through internal aperture 420 and into aperture 316 on surface 322 and may also guide a Kirschner wire (K wire) or a drill. Proximal screw member 130, of FIG. 2, travels into bone as portions 216 and 206 travel further through aperture 316 at end 302 until bulbous portion 202 is restrained by surface 322 and end 302. Aperture 316, being tapered along axis 303, causes proximal screw member 130 to form an angle 150 with distal member 140, with proximal member 130 being aligned along an axis 303, which is substantially the same axis as axis 403 of tubular portion 412 of instrument 120.

Figure 5:
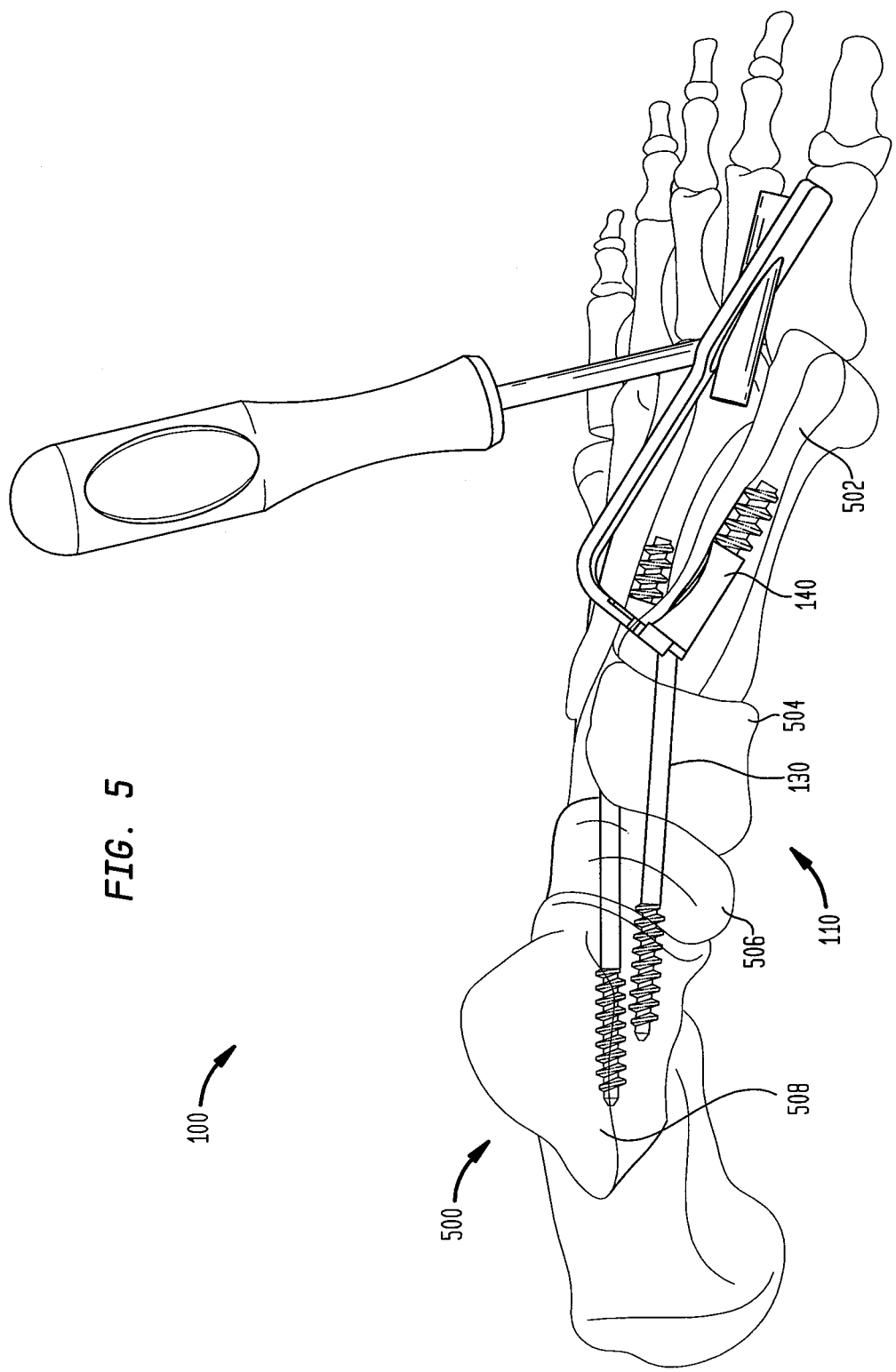
FIG. 5 is a perspective view of the assembled intramedullary fixation assembly inserted into the bones of a patient's foot according to the preferred embodiment of the invention.
Figure 6:
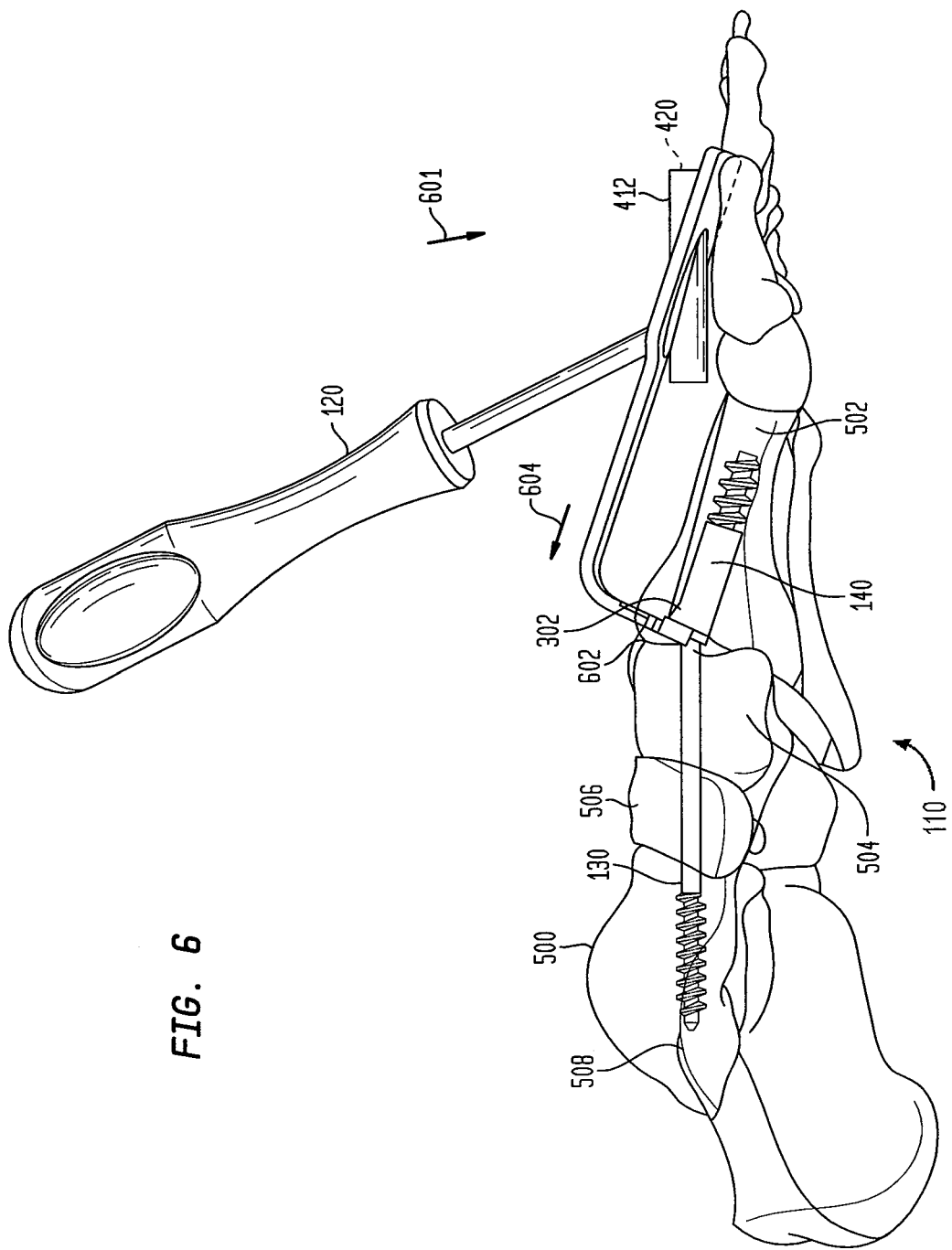
FIG. 6 is a side view of the assembled intramedullary fixation assembly shown in FIG. 5 according to the preferred embodiment of the invention.
Figure 7:
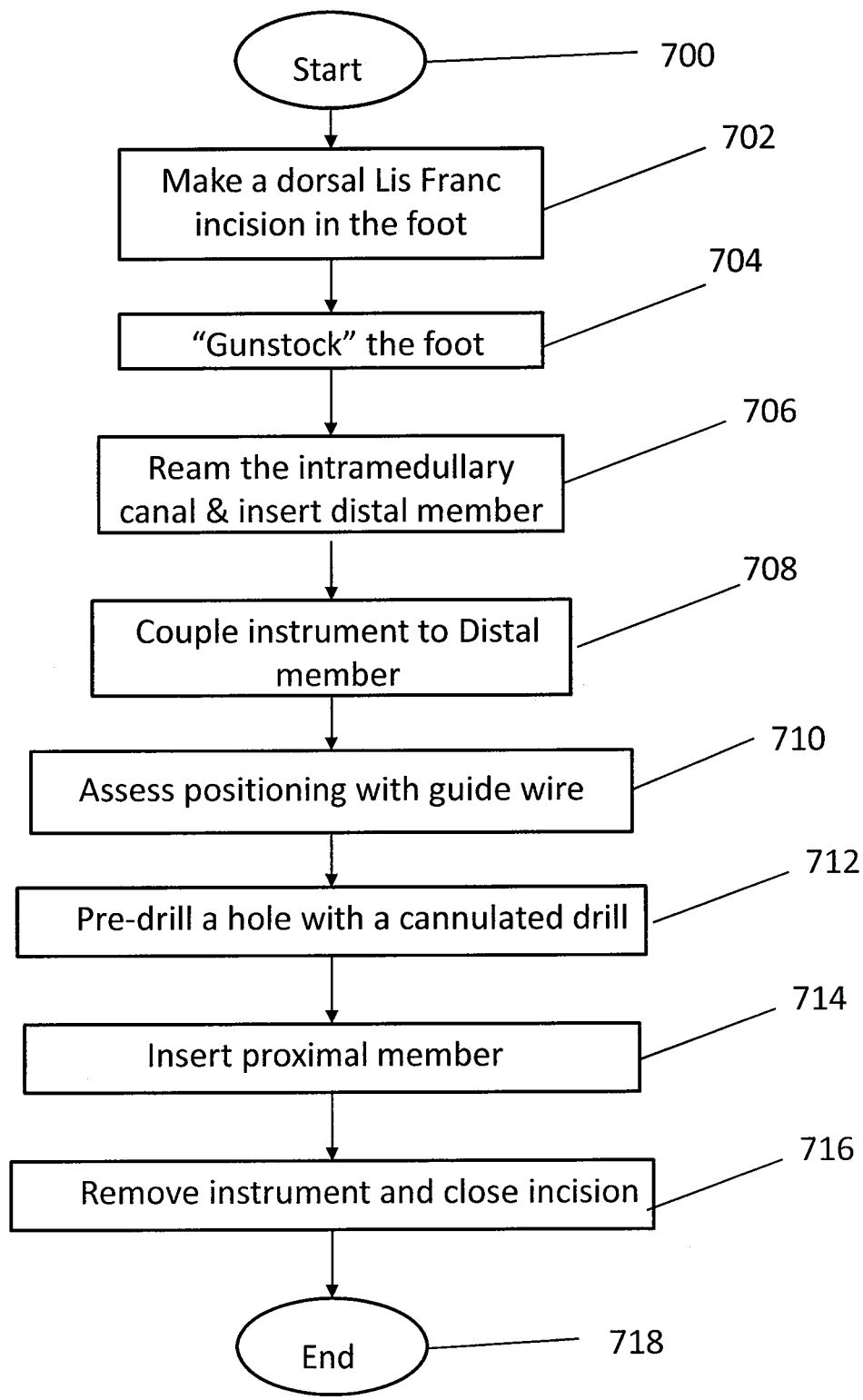
FIG. 7 is a flow chart illustrating the method of coupling the intramedullary fixation assembly shown in FIGS. 1-6 to tarsal and metatarsal bones in a patient's foot according to the preferred embodiment of the invention.

In operation, and as best shown in FIGS. 5, 6 and 7, the fixation system 100 utilizes the intramedullary fixation assembly 110 for treating and fixating the deteriorated and damaged or fractured bones in the human foot 500. This restores the arch in a human foot 500 by coupling the intramedullary fixation assembly 110 to the human foot 500 of a left leg. In one-non limiting example, and as shown in FIG. 5, the intramedullary assembly 110 is coupled to the medullary canals of the first metatarsal 502, medial cuneiform 504, navicular 506 and talus bone 508. Talus bone 508 makes up part of the ankle joint where the threaded portion 216 of the proximal screw member 130 of the intramedullary assembly 110 is threadably coupled. The medial cuneiform 504 and navicular 506 bones are most affected by Diabetic Charcot foot disorder that causes deterioration and collapse of the arch of the foot 500. It should be appreciated that the intramedullary assembly 110 may be used within each of the five rays, with a ray representing a line drawn from each metatarsal bone to the talus. The angulation in the smaller rays will be smaller than the two rays (i.e., a line from the first and second metatarsal bones to the talus bone). Also, the diameter of distal member 140 will decrease from the large ray to the small ray. In one non-limiting example, the angulation may be any angle greater than 90 degrees and less than 180 degrees. For example, the angle for the first ray may be 150-170 degrees and the angles for the other rays may be 160-175 degrees.

As shown in FIGS. 6 and 7, the intramedullary fixation assembly 110 may be utilized to reconstruct an arch in a mid-foot region of a human foot 500. As shown, the method starts in step 700 and proceeds to step 702, whereby a Dorsal Lis Franc incision (i.e., mid-foot incision) (not shown) is made in foot 500 in order to gain access to the joint. In step 704, the joint capsule is separated by "Gunstocking" foot 500 in direction 601 (i.e., the foot 500 is bent mid-foot) to expose the articular surface 602 and the articulating cartilage is removed. Next, in step 706, the intramedullary canal is reamed and the distal member 140 is inserted into the intramedullary canal (not shown) of the metatarsal 502. In other non-limiting embodiments, the distal member 140 may be inserted by impaction, by press fit, by reaming a hole in the intramedullary canal (not shown) or substantially any other similar strategy or technique.

Next, in step 708, the instrument 120 is coupled to the distal member 140 by coupling sides 426 and 428 of instrument 120 to respective grooves 326 and 328. In step 710, initial positioning of the proximal member 130 is assessed with the use of a guide wire through portion 412 (i.e., aiming device). Next, in step 712, a countersink drill is inserted through portion 412 and the proximal cortex is penetrated. In this step, a cannulated drill or guide wire is used to pre-drill the hole through the joints selected for fusion. In step 714, the proximal screw member 130 is inserted over the guide wire and into the distal member 140. Particularly, the proximal member 130 is inserted through tubular portion 412 (i.e., aiming device), causing proximal member 130 to travel through internal longitudinal aperture 420, into distal member 140 and further into bones 504, 506 and 508 until rigid connection with the tapered aperture 316 is made, thereby compressing the joint. In one non-limiting embodiment, a locking element (not shown) such as a plate or a washer is coupled to end 302 of the intramedullary fixation assembly 110 to further secure proximal threaded member 130 to distal member 140. Next, in step 716 the instrument 120 is removed and the dorsal Lis Franc (i.e., mid-foot) incision is closed. The method ends in step 718.

It should be appreciated that a plurality of intramedullary fixation assemblies, such as intramedullary fixation assembly 110, may be inserted into any of the bones of a foot 500 such as, but not limited to the metatarsal, cuneiform, calcaneus, cuboid, talus and navicular bones, in order to restore the natural anatomical shape of the arch of the foot 500. Thus, the fixation system 100, in one non-limiting embodiment, is utilized to couple the intramedullary fixation assembly 110 to the foot 500, which causes the metatarsal 504, medial cuneiform 504, navicular 506 and talus 508 bones to be aligned to the proper anatomical shape of an arch when assembled within foot 500. It should be appreciated that the intramedullary fixation assembly 110 is delivered through a dorsal midfoot incision, thereby reducing the disruption to the plantar tissues and/or the metatarsal heads while at the same time minimizing the tension on the skin. This allows for improved wound closure, reduced operating room time, reduction in the number of incisions required and reduction in the total length of incisions. It should also be appreciated that in other non-limiting embodiments, the intramedullary assembly 110 may be utilized with graft material (i.e., autograft, allograft or other biologic agent).

Figure 8:
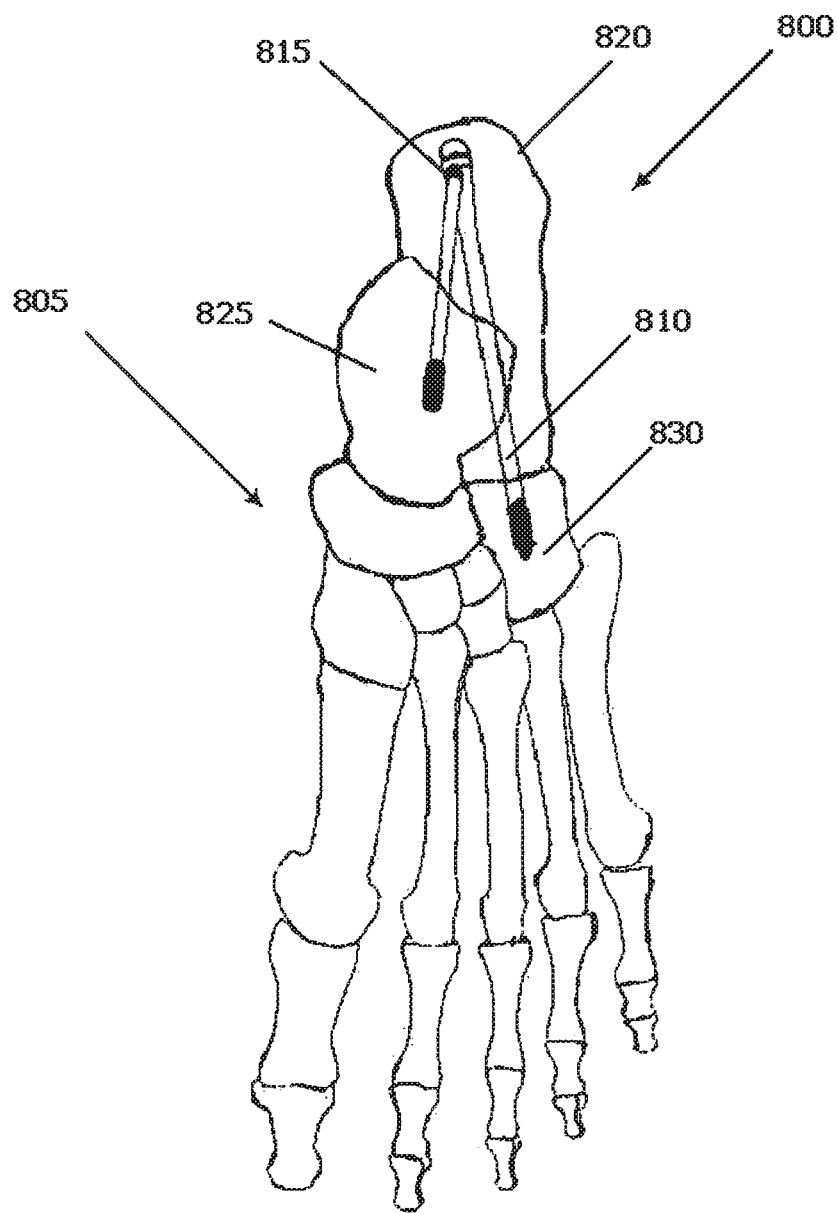
FIG. 8 is a perspective view of an assembled intramedullary fixation assembly inserted into the bones of a patient's foot according to an alternate embodiment of the invention.

In an alternate embodiment, as shown in FIG. 8, an intramedullary fixation assembly 800 is provided in order to apply intraosseous compression to bones. Particularly, the intramedullary fixation assembly 800 comprises a tapered screw member 810 coupled to a lag screw member 815 at a fixed acute angle for the internal fusion of the bones of the human foot 805, such as, for example, the calcaneus bone 820, the talus bone 825, and the cuboid bone 830. In other non-limiting embodiments, the intramedullary fixation assembly 800 may be utilized for any other appropriate use for the internal fixation of the other bones. It should be appreciated that the intramedullary fixation assembly 800 may be provided at several lengths for the internal fixation of a variety of bone sizes in the human body.

Figure 9:
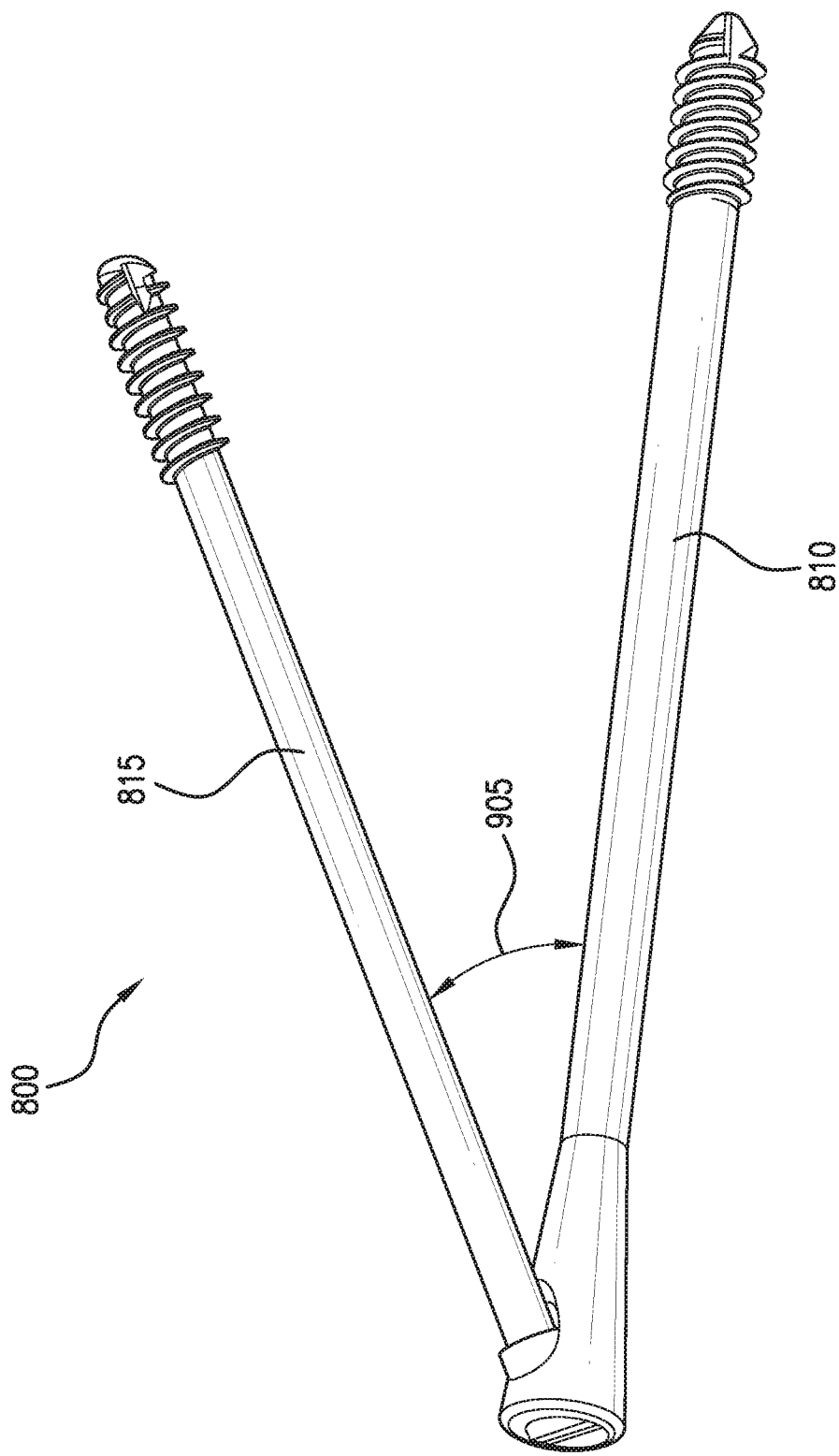
FIG. 9 is a perspective view of the intramedullary fixation assembly shown in FIG. 8 according to the alternate embodiment of the invention.

Also as shown in FIG. 9, the intramedullary fixation assembly 800 includes the tapered screw member 810 coupled to the lag screw member 815 at a fixed angle 905. The fixed angle 905 may be provided at various fixed angles depending on the bone segments that are being compressed. The fixed angle between the tapered screw member 810 and the lag screw member 815 causes the intramedullary fixation assembly 800 to "hook" into the bone segments and translates the compression applied to bone fragments across the members 810 and 815. It should be appreciated that in one non-limiting embodiment, the intramedullary fixation assembly 800 may be made from a Titanium material, although, in other non-limiting embodiments, the intramedullary fixation assembly 800 may be made from SST, PEEK, NiTi, Cobalt chrome or other similar types of materials. It should also be appreciated that the intramedullary fixation assembly 800 is locked at the fixed angle after insertion of the same into bone. The intramedullary fixation assembly 800 translates compression applied to bone fragments by the tapered screw member 810 and the lag screw member 815 into uniform compression through multi-point fixation.

Figure 10:
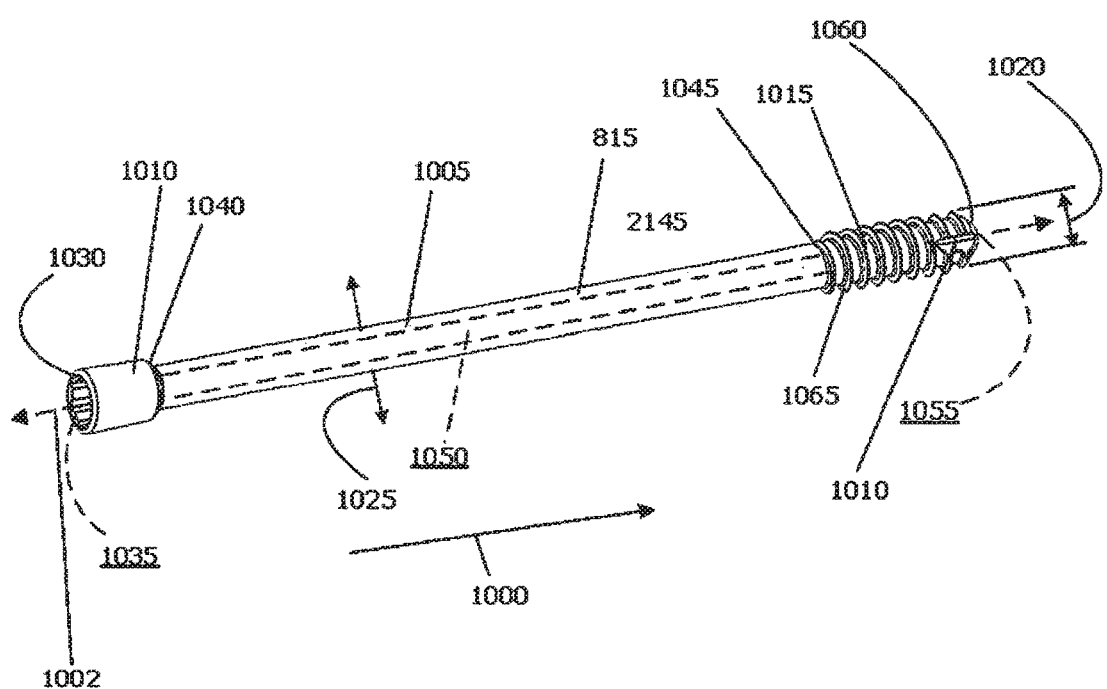
FIG. 10 is a perspective view of the lag screw member used in the intramedullary fixation assembly shown in FIGS. 8-9 according to the alternate embodiment of the invention.

As shown in FIG. 10, lag screw member 815 is generally cylindrical in shape and has a first smooth exterior portion 1005 that extends from first bulbous portion 1010 to a second threaded portion 1015. Additionally, bulbous portion 1010 has a taper, such as a Morse taper, with a width that decreases from end 1030 in direction 1000. The Morse taper allows for a locked interference fit with tapered aperture 1130 (shown in FIG. 11) when tapered bulbous portion 1010 resides within tapered aperture 1130, which will be shown and described below. Moreover, tapered bulbous portion 1010 is generally cylindrical in shape and has a generally hexagonal-shaped aperture 1035 aligned along axis 1002 traversing the longitudinal length of bulbous portion 1010. However, a star-shaped aperture, a square-shaped aperture, or any other shaped aperture may be utilized without departing from the scope of the invention. Aperture 1035 is provided to transmit torque from bulbous portion 1010 to threaded portion 1015 as bulbous portion 1010 is rotated in a direction that causes a corresponding rotation of threaded portion 1015.

Further, lag screw member 815 has a first smooth exterior portion 1005 that has a uniform diameter 1025 from first end 1040 to second end 1045. Portion 1005 includes an internal aperture 1050 aligned along axis 1002 that traverses the longitudinal length of portion 1005 in direction 1000. Further, portion 1005 terminates into a threaded portion 1015. Threaded portion 1015 includes an internal aperture 1055 aligned along axis 1002 that longitudinally traverses threaded portion 1015. Internal aperture 1055 being aligned on the same axis 1002 as apertures 1035 and 1055 cooperatively form a continuous opening (i.e., a cannula) from end 1030 of bulbous portion 1010 to end 1060 of threaded portion 1015. The continuous opening or cannula is provided to interact with a guide wire (not shown) by receiving the guide wire within the continuous opening to help guide and position the lag screw member 815 during insertion of the lag screw member 815. In other non-limiting embodiments, the lag screw member 815 may be provided without apertures 1050 and 1055 (i.e., the lag screw member 815 is solid).

Furthermore, threaded portion 1015 has a plurality of circular threads, such as threads 1065, which are circumferentially disposed on the external surface of threaded portion 1015. Threaded portion 1015 has a diameter 1020 that is substantially the same as diameter 1025 of portion 1005. Threaded portion 1015 may also be provided with a self-tapping leading edge 1070 to provide portion 1015 with the ability to remove bone material during insertion of lag screw member 815 into bone. It should be appreciated that the length of the lag screw member 815 may be selected of varying lengths to allow a surgeon to fuse different joints in the human body. It should be appreciated that the lag screw member 815 may be positioned at one angle inside the tapered screw member 810. Also, lag screw member 815 may be coated with an osteoconductive material, such as, for example, plasma spray or other similar types of porous materials that is capable of supporting or encouraging bone ingrowth into this material.

Figure 11:
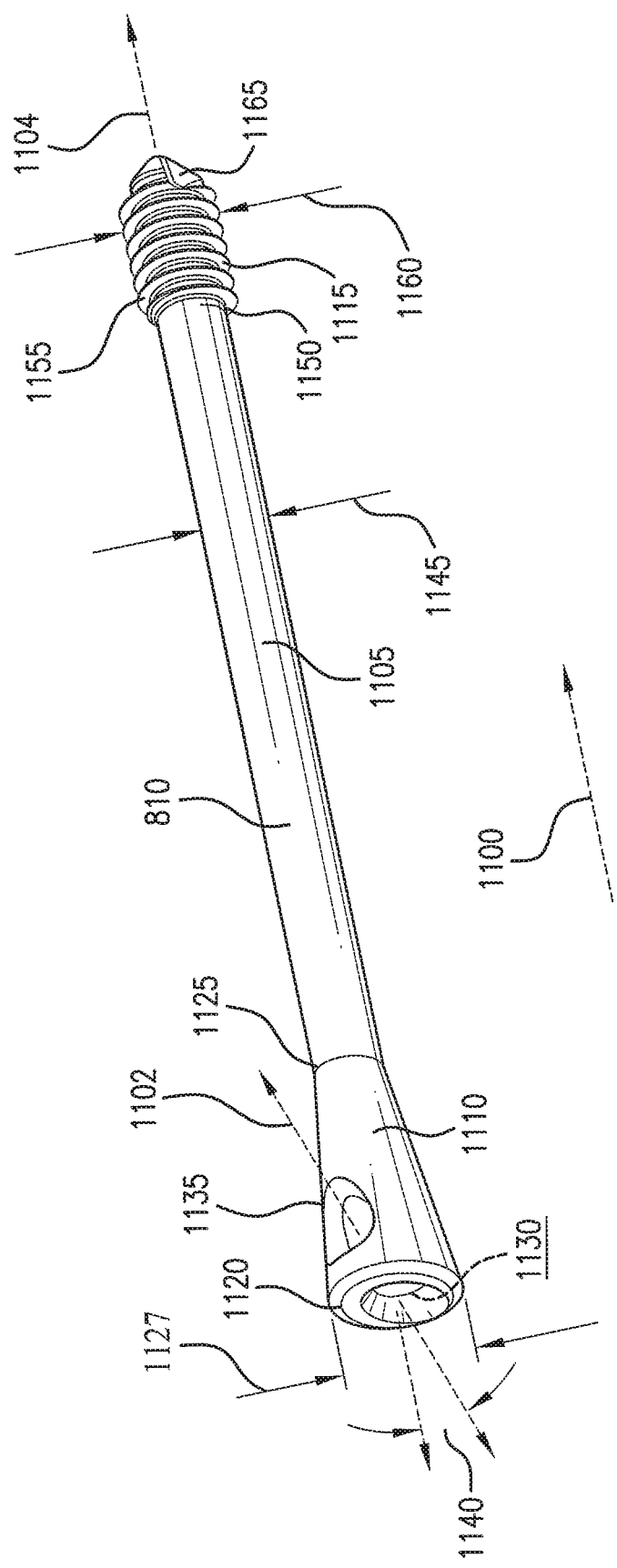
FIG. 11 is a perspective view of the tapered screw member used in the intramedullary fixation assembly shown in FIGS. 8-9 according to the alternate embodiment of the invention.

As shown in FIG. 11, tapered screw member 810 is generally cylindrical in shape and has a smooth exterior portion 1105 that extends from a tapered portion 1110 to a threaded portion 1115. Tapered screw member 810 is aligned along longitudinal axis 1104, which is longitudinally coextensive with length of tapered screw member 810.

Further, tapered portion 1110 is generally tubular in shape and tapers from end 1120 to end 1125 (i.e. end 1120 has a diameter 1127 that decreases slightly in diameter from end 1120 in direction 1100). Further, first end 1120 has a tapered aperture 1130, which traverses tapered portion 1110 along axis 1102, which causes tapered aperture 1130 to emanate from surface 1135. Axis 1102 is offset from longitudinal axis 1104 at an angle 1140. Moreover, tapered portion 1110 has a generally hexagonal-shaped aperture contained within portion 1110, which is aligned along axis 1104 and is provided to receive an instrument (not shown) for applying torque to tapered screw member 810. In other non-limiting embodiments, a star-shaped aperture, a square-shaped aperture, or any other shaped aperture may be utilized without departing from the scope of the invention. With tapered aperture 1130 being aligned along axis 1102, tapered aperture 1130 forms a fixed angle 1140 with longitudinal axis 1145. Fixed angle 1140 determines the angle for fixation of tapered screw member 810 with respect to lag screw member 815 (shown in FIG. 10). It should be appreciated that fixed angle 1140 may be any angle less than 90 degrees to allow a surgeon the flexibility of determining the angle for internal fixation of bones in the human body. It should also be appreciated that tapered aperture 1130 when combined with tapered bulbous portion 1010, shown in FIG. 10, creates a locked interference fit between tapered screw member 810 and lag screw member 815.

Further, tapered screw member 810 has a smooth exterior portion 1105 that has a uniform diameter 1145 from end 1125 to end 1150. Tapered screw member 810 is generally solid, however, in other non-limiting embodiments, screw member 810 may be cannulated. Further, portion 1105 terminates into a threaded portion 1115. Threaded portion 1115 is generally solid and includes a plurality of circular threads, such as threads 1155, which are circumferentially disposed on the external surface of threaded portion 1115. Threaded portion 1115 has a diameter 1160 that is substantially the same as diameter 1145 of portion 1105. Threaded portion 1115 may also be provided with a self-tapping leading edge 1165 to provide portion 1115 with the ability to remove bone material during insertion of tapered screw member 810 into bone. It should be appreciated that the length of the tapered screw member 810 may be selected of varying lengths to allow a surgeon to fuse different joints in the human body. It should be appreciated that tapered screw member 810 may be coated with an osteoconductive material, such as, for example, plasma spray or other similar types of porous materials that is capable of supporting or encouraging bone ingrowth into this material.

Figure 12:
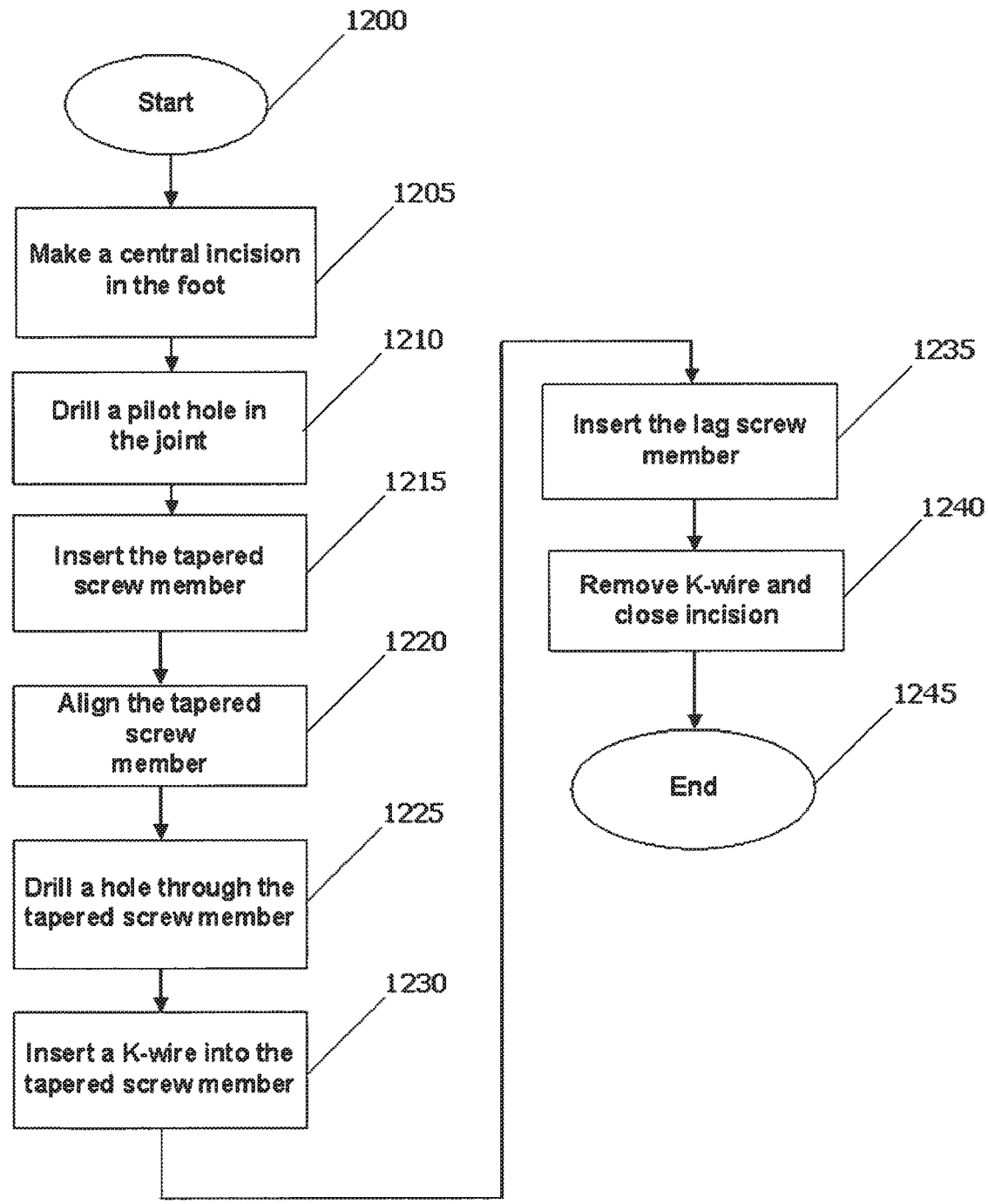
FIG. 12 is a flow chart illustrating the method of coupling the intramedullary fixation assembly shown in FIG. 8-9 to bones in a patient's foot according to the alternate embodiment of the invention.

As shown in FIGS. 8 and 12, the intramedullary fixation assembly 800 may be utilized to apply compression, for example to the bones in a human foot through an acute angle fixation of the tapered screw member 810 to the lag screw member 815. As shown, the method starts in step 1200 and proceeds to step 1205, whereby a central incision is made in the hind-foot region of foot 805. Next, in step 1210, a pilot hole is drilled into the calcaneus 820 and the cuboid 830 bones. In this step, a countersink drill is inserted a cannulated drill or guide wire is used to pre-drill the hole through the joints selected for fusion. Next, in step 1215, tapered screw member 810 is inserted into the intraosseous intramedullary canal (not shown) of the calcaneus 820. In other non-limiting embodiments, the tapered screw member 810 may be inserted by impaction, by press fit, by reaming a hole in the intramedullary canal (not shown) or substantially any other similar strategy or technique.

Next, in step 1220, the final position of the tapered screw member 810 is aligned so that the coupling of the lag screw member 815 forms a predetermined angle with the tapered screw member 810. In step 1225, align a guide through tapered aperture 1130 at surface 1135 and pre-drill a hole through the joint substantially along axis 1102. Next, in step 1230, insert a K-wire (not shown) into the pre-drilled hole and into the tapered screw member 810 so that the K-wire makes an acute angle with the tapered screw member 810. Next, in step 1235, the lag screw member 815 is rotated and inserted over the K-wire and into the calcaneus bone 820 so that the K-wire guides the lag screw member 815. The K-wire, in assisting the lag screw member 815, penetrates end 1060 and emanates from end 1030. In some non-limiting embodiments, the lag member 815 may be inserted by impaction, by press fit, or substantially any other similar strategy or technique. Next, in step 1240, the K-wire is removed and the incision is closed. The method ends in step 1245.

Figure 13:
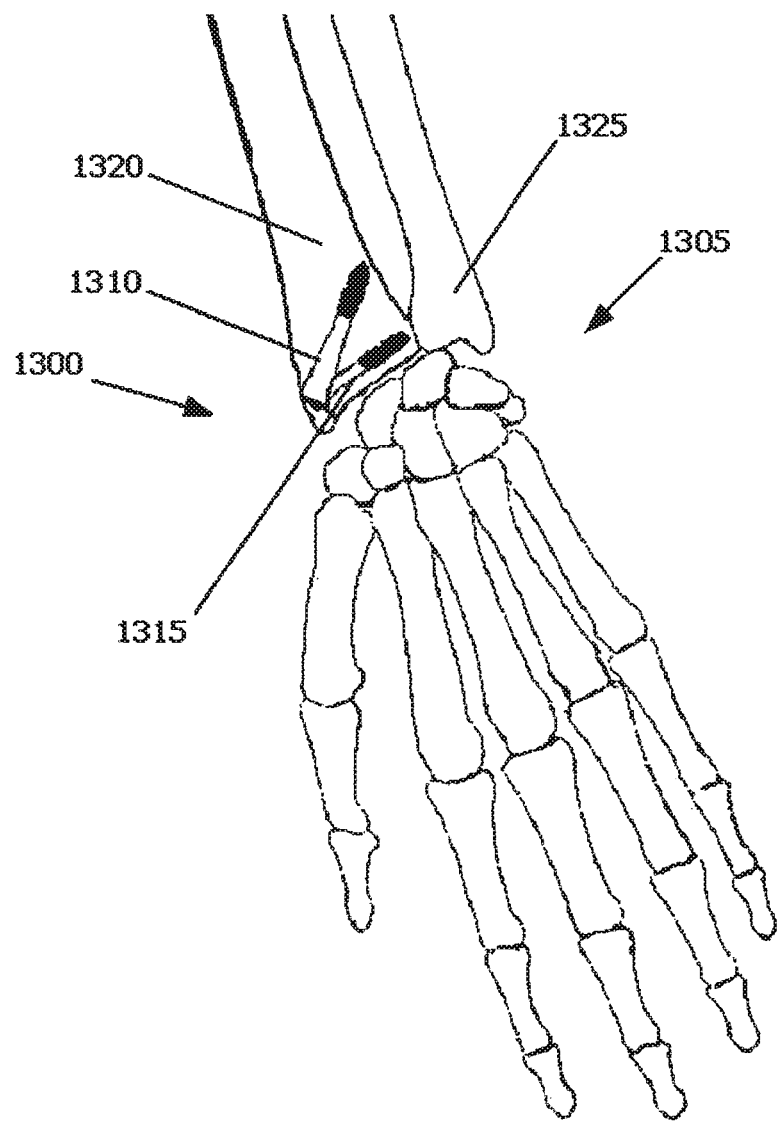
FIG. 13 is a perspective view of an assembled intramedullary fixation assembly inserted into the bones of a patient's hand according to an alternate embodiment of the invention.

In an alternate embodiment, as shown in FIG. 13, an intramedullary fixation assembly 1300 is provided for the internal fixation of bones in a human hand 1305. Particularly, the intramedullary fixation assembly 1300 is substantially the same as the intramedullary fixation assembly 800 of the embodiment shown and described in FIG. 8. The intramedullary fixation assembly 1300 includes a tapered screw member 1310 forming a fixed acute angle with the lag screw member 1315. The fixed acute angle is predetermined and the angle may be selected up to 90 degrees by, in one example, a surgeon to provide for the internal fixation of the bones in the human hand 1305, such as for example the radius 1320 and ulna 1325.

Figure 14:
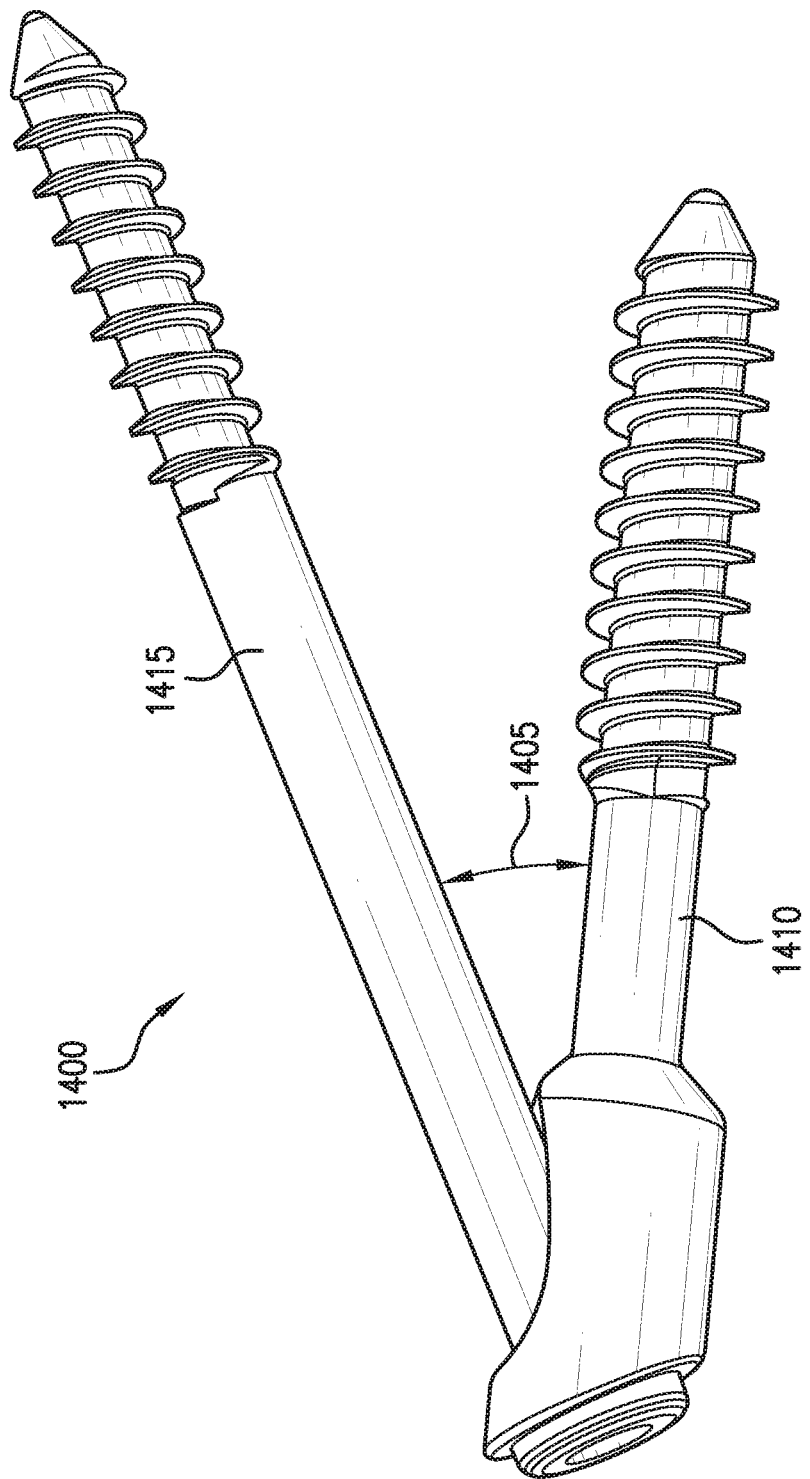
FIG. 14 is a perspective view of the intramedullary fixation assembly shown in FIG. 13 according to the alternate embodiment of the invention.

In another alternate embodiment, as shown in FIG. 14, an intramedullary fixation assembly 1400 may be provided to vary the acute angle between 0 and 90 degrees after insertion of the intramedullary fixation assembly 1400. Particularly, the intramedullary fixation assembly 1400 comprises a polyaxial screw member 1410 coupled to a lag screw member 1415 and forming an angle 1405 between the two members 1410 and 1415. The angle 1405 between the polyaxial screw member 1410 and the lag screw member 1415 causes the intramedullary fixation assembly 1400 to "hook" into the bone segments and translates the compression applied to bone fragments across the members 1410 and 1415. It should be appreciated that the intramedullary fixation assembly 1400 may be provided at several lengths for the internal fixation of a variety of bone sizes in the human body. It should also be appreciated that in one non-limiting embodiment, the intramedullary fixation assembly 1400 may be made from a Titanium material, although, in other non-limiting embodiments, the intramedullary fixation assembly 1400 may be made from SST, PEEK, NiTi, Cobalt chrome or other similar types of materials.

Figure 15:
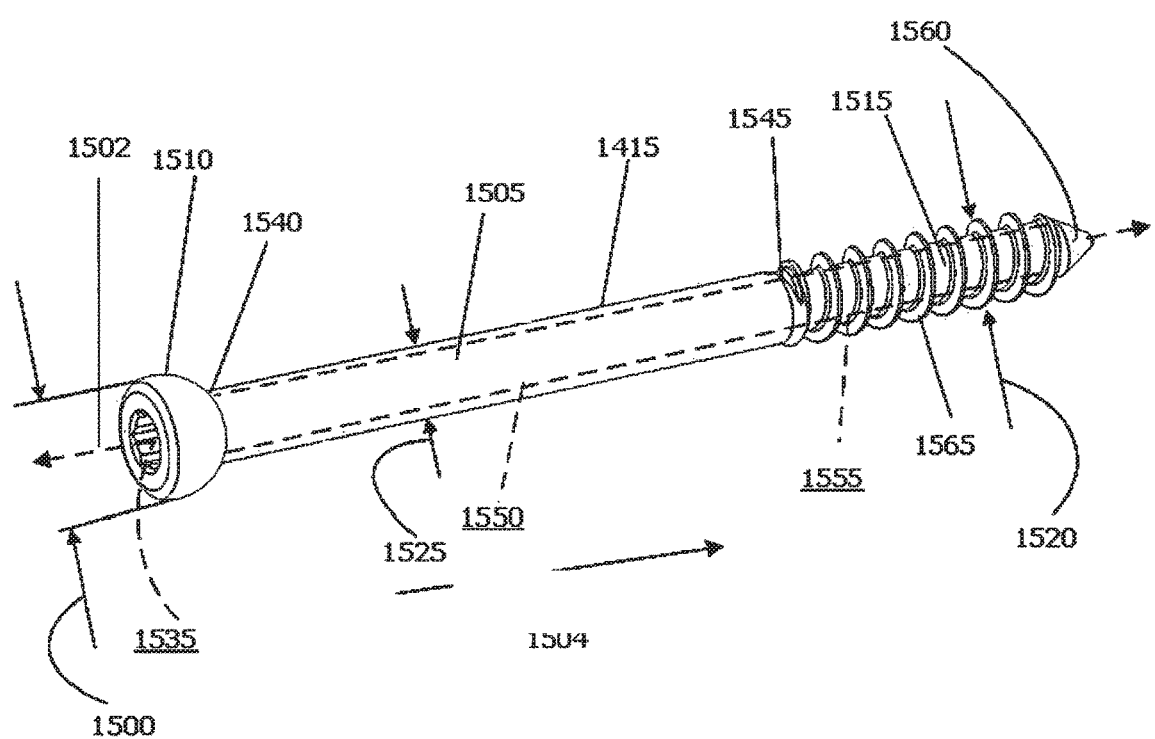
FIG. 15 is a perspective view of the lag screw member used in the intramedullary fixation assembly shown in FIG. 14 according to the alternate embodiment of the invention.

As shown in FIG. 15, lag screw member 1415 is generally cylindrical in shape and has a first smooth exterior portion 1505 that extends from first bulbous portion 1510 to a second threaded portion 1515. Bulbous portion 1510 is generally semispherical in shape and has a diameter 1500 that is slightly larger than the internal diameter of aperture 1630 (shown in FIG. 16), which is provided to receive bulbous portion 1510. The bulbous portion 1510 resides within the internal aperture 1630 (shown in FIG. 16) and provides for rotational movement of both the polyaxial screw member 1410 and the lag screw member 1415 at various angles between 0 and 90 degrees after insertion of the intramedullary fixation assembly 1400. Also, bulbous portion 1510 has a generally hexagonal-shaped aperture 1535 aligned along axis 1502 traversing the longitudinal length of bulbous portion 1510. In other non-limiting embodiments, a star-shaped aperture, a square-shaped aperture, or any other shaped aperture may be utilized without departing from the scope of the invention. Aperture 1535 is provided to transmit torque from bulbous portion 1510 to threaded portion 1515 as bulbous portion 1510 is rotated in a direction that causes a corresponding rotation of threaded portion 1515. It should also be appreciated that axis 1502 is longitudinally coextensive with the length of lag screw member 1415.

Further, lag screw member 1415 has a first smooth exterior portion 1505 of a uniform diameter 1525 from first end 1540 to second end 1545. Portion 1505 includes an internal aperture 1550 aligned along axis 1502 that traverses the longitudinal length of portion 1505 along direction 1504. Further, portion 1505 terminates into the threaded portion 1515. Threaded portion 1515 also includes an internal aperture 1555 aligned along axis 1502 that longitudinally traverses threaded portion 1515. Internal aperture 1555 being aligned along the same axis 1502 as apertures 1535 and 1550 cooperatively form a continuous opening (i.e., a cannula) from bulbous portion 1510 to end 1560 of threaded portion 1515. The continuous opening or cannula is provided to interact with a guide wire (not shown) by receiving the guide wire within the continuous opening to help guide and position the lag screw member 1415 during insertion into bone. In other non-limiting embodiments, the lag screw member 1415 may be provided without apertures 1550 and 1555 (i.e., the lag screw member 1415 is non-cannulated or solid).

Furthermore, threaded portion 1515 has a plurality of circular threads, such as threads 1565, which are circumferentially disposed on the external surface of threaded portion 1515. Threaded portion 1515 has a diameter 1520 that is substantially the same as diameter 1525 of portion 1505. Threaded portion 1515 may also be provided with a self-tapping leading edge (not shown) to provide portion 1515 with the ability to remove bone material during insertion of lag screw member 1415 into bone. It should be appreciated that the length of the lag screw member 1415 may be selected of varying lengths to allow a surgeon to fuse different joints in the human body. Also, lag screw member 1415 may be coated with an osteoconductive material, such as, for example, plasma spray or other similar types of porous materials that is capable of supporting or encouraging bone ingrowth into this material.

Figure 16:
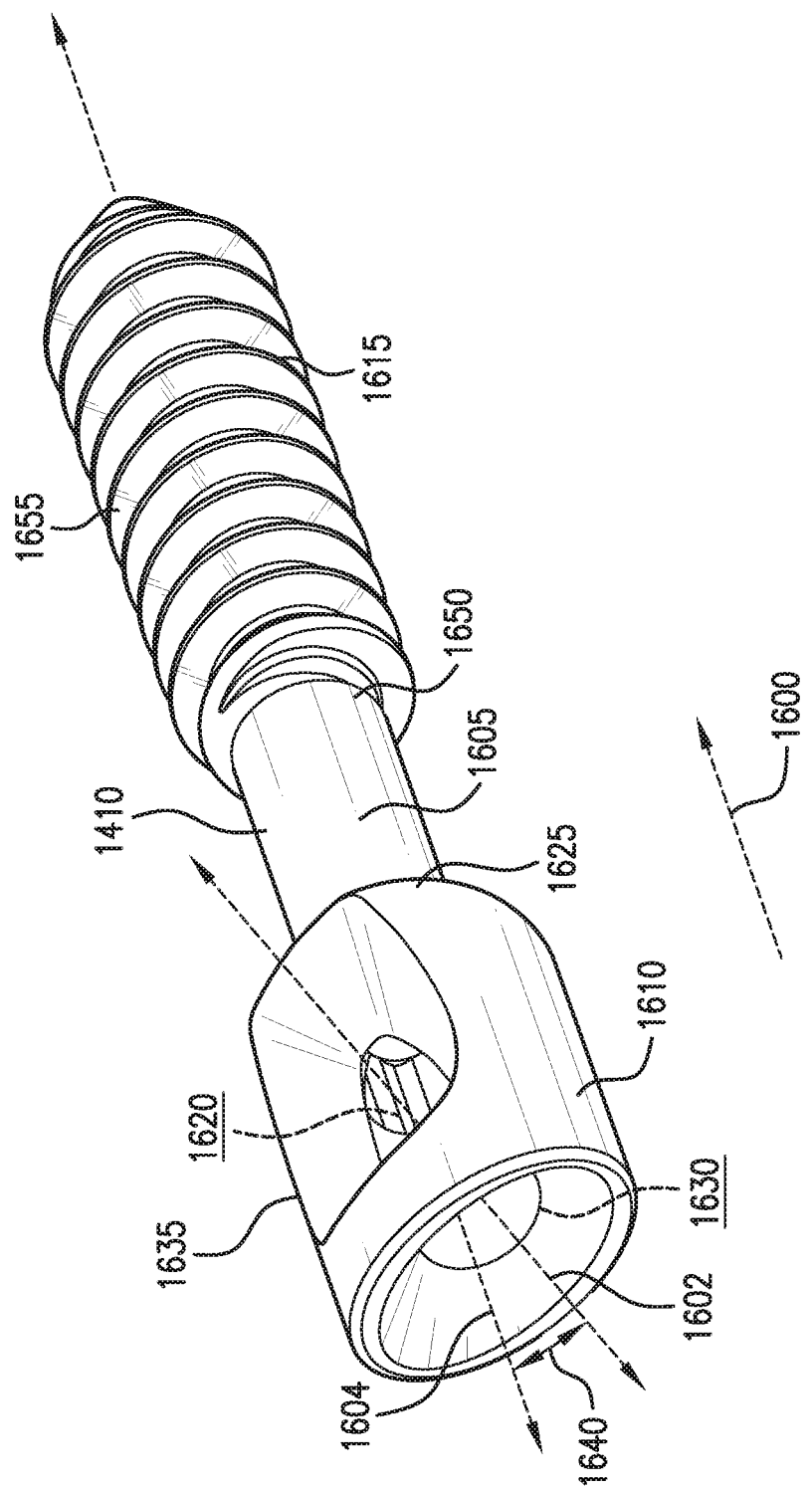
FIG. 16 is a perspective view of the polyaxial screw member used in the intramedullary fixation assembly shown in FIG. 14 according to the alternate embodiment of the invention.

As shown in FIG. 16, polyaxial screw member 1410 is generally cylindrical in shape and has a smooth exterior portion 1605 that extends from portion 1610 to a threaded portion 1615. Polyaxial screw member 1410 is aligned along longitudinal axis 1604, which is longitudinally coextensive with length of polyaxial screw member 1410.

Further, portion 1610 is generally tubular in shape having a uniform diameter, which is slightly larger than diameter of aperture 1630 causing portion 1610 to abut the interior surface of portion 1610 at aperture 1630. However, in other non-limiting embodiments, portion 1610 may be tapered going from a larger diameter to a smaller diameter as we traverse portion 1610 along direction of axis 1600. Further, portion 1610 has a plurality of apertures 1620 and 1630 of dissimilar diameters. Aperture 1630 is a through aperture and is tapered along axis 1602, causing aperture 1630 to emanate from surface 1635. On the other hand, aperture 1620 is longitudinally disposed along axis 1604 and has a generally hexagonal shaped aperture, although in other non-limiting embodiments, a star-shaped aperture, a square-shaped aperture, or any other shapes aperture may be utilized. Aperture 1630 is offset from axis 1604 at an angle 1640. Angle 1640 determines the angle for rotation of lag screw member 1415 when bulbous portion 1510 (shown in FIG. 15) resides in aperture 1630 with lag screw member 1415 rotating angularly around axis 1602. It should be appreciated that angle 1640 may be any angle less than 90 degrees to allow a surgeon the flexibility of fixing the rotation of polyaxial screw member 1410 and lag screw member 1415.

Further, polyaxial screw member 1410 has a smooth exterior portion 1605 having a uniform diameter from end 1625 to end 1650. The diameter of exterior portion 1605 is smaller than the diameter of aperture 1630. Polyaxial screw member 1410 is generally solid, however, in other non-limiting embodiments, polyaxial screw member 1410 may be cannulated. Further, portion 1605 terminates into a threaded portion 1615. Threaded portion 1615 is generally solid and includes a plurality of circular threads, such as threads 1655, circumferentially disposed on the external surface of threaded portion 1615. Threaded portion 1615 has a uniform diameter that is slightly larger than the diameter of portion 1605. However, in other non-limiting embodiments, the respective diameters of portions 1605 and 1615 may be substantially the same. Threaded portion 1615 may also be provided with a self-tapping leading edge (not shown) to provide portion 1615 with the ability to remove bone material during insertion of polyaxial screw member 1410 into bone. It should be appreciated that the length of the polyaxial screw member 1410 may be selected of varying lengths to allow a surgeon to fuse different joints in the human body. It should be appreciated that polyaxial screw member 1410 may be coated with an osteoconductive material, such as, for example, plasma spray or other similar types of porous materials that is capable of supporting or encouraging bone ingrowth into this material.

Figure 17:
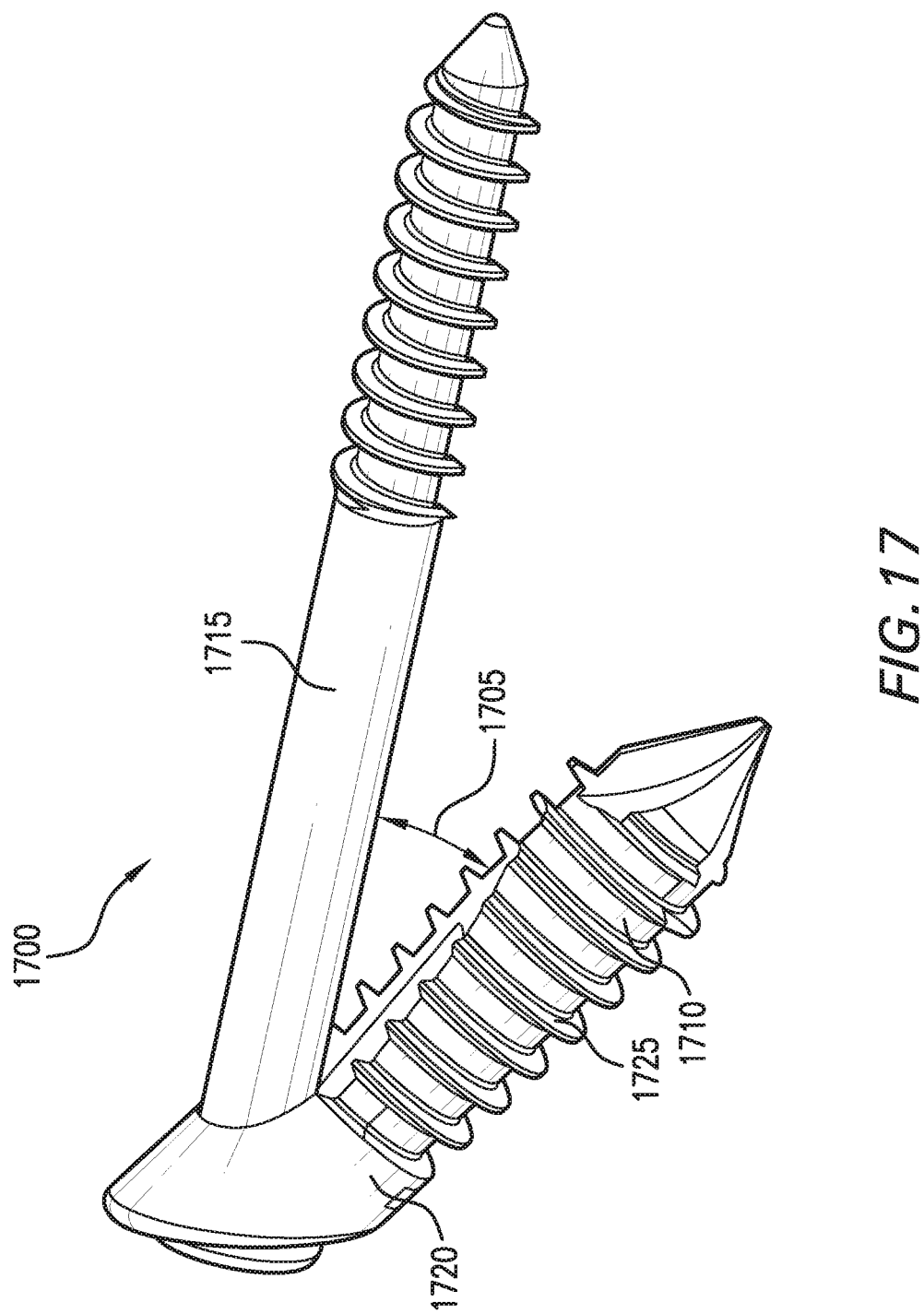
FIG. 17 is a perspective view of an assembled intramedullary fixation assembly according to an alternate embodiment of the invention.

In another alternate embodiment, as shown in FIG. 17, length of the polyaxial screw member 1710 may be varied in order to accommodate the intramedullary fixation assembly 1700 in bones of various sizes. Particularly, the polyaxial screw member 1710 includes a smooth end portion 1720 coupled directly to a threaded portion 1725, thereby varying the angle 1705 that is formed between the polyaxial screw member 1710 and the lag screw member 1715. In all other respects, the intramedullary fixation assembly 1700 is substantially similar to the intramedullary fixation assembly 1400 as was shown and described in FIG. 14.

Figure 18:
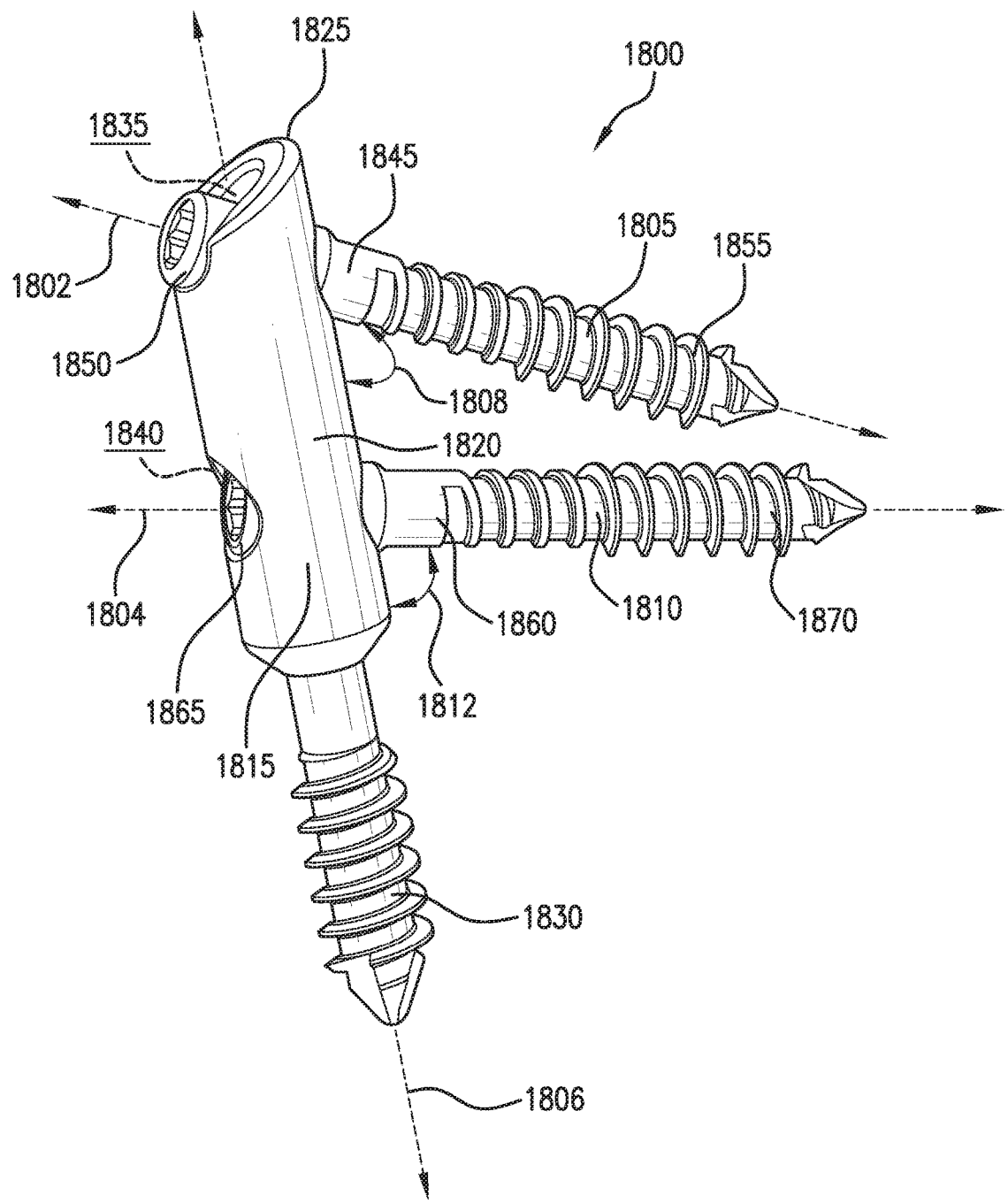
FIG. 18 is a perspective view of an assembled intramedullary fixation assembly having a plurality of lag screw members according to an alternate embodiment of the invention.

In another alternate embodiment, as shown in FIG. 18, an intramedullary fixation assembly 1800 having a plurality of lag screw members 1805 and 1810 coupled to a tapered screw member 1815 is provided in order to apply compression at multiple points on the bone fragment surface. Particularly, the lag screw members 1805 and 1810, and the tapered screw member 1815 are substantially similar to the lag screw member 815 and tapered screw member 810 respectively shown and described in the embodiment of FIGS. 8-11. Each of the lag screw members 1805 and 1810 forms an fixed acute angle with the tapered screw member 1815, with these angles being predetermined by, for example, a surgeon to fix the bones in a human body.

As shown, tapered screw member 1815 is generally cylindrical in shape and has a smooth exterior portion 1820 that extends longitudinally along axis 1806 from end 1825 to a threaded portion 1830. Further, end 1825 has a tapered aperture 1835, which is aligned on axis 1802 and forms a fixed angle 1808 with axis 1806. Fixed angle 1808 determines the angle for fixation of tapered screw member 1810 with respect to lag screw member 1805. Also, tapered screw member 1815 has a second tapered aperture 1840, aligned along axis 1804 and forms a fixed angle 1812 with axis 1804. The fixed angle 1812 determines the angle for fixation of lag screw member 1810 with tapered screw member 1815. It should be appreciated that fixed angles 1808 and 1812 may be any angle less than 90 degrees to allow a surgeon the flexibility of determining the angle for internal fixation of bones in the human body. It should also be appreciated that tapered screw member 1815 creates a locked interference fit with each of the lag screw members 1805 and 1810.

Further, tapered screw member 1815 has a smooth exterior portion 1820 having a uniform diameter from end 1825 to threaded portion 1830. Tapered screw member 1815 is generally solid, however, in other non-limiting embodiments, screw member 1815 may be cannulated. Further, threaded portion 1830 is generally solid and includes a plurality of circular threads circumferentially disposed on the external surface of threaded portion 1830. Threaded portion 1830 may also be provided with a self-tapping leading edge to provide portion 1830 with the ability to remove bone material during insertion of tapered screw member 1815 into bone. It should be appreciated that the length of the tapered screw member 1815 may be selected of varying lengths to allow a surgeon to fuse different joints in the human body. It should be appreciated that tapered screw member 1815 may be coated with an osteoconductive material, such as, for example, plasma spray or other similar types of porous materials that is capable of supporting or encouraging bone ingrowth into this material.

Also as shown in FIG. 18, each of the respective lag screw members 1805 and 1810 are substantially similar to the lag screw member of the embodiment shown and described in FIG. 10. Particularly, lag screw member 1805 is generally cylindrical in shape and has a first smooth exterior portion 1845 that extends from bulbous portion 1850 to a threaded portion 1855, while lag screw member 1810 has a smooth exterior portion 1860 that extends from bulbous portion 1865 to threaded portion 1870. Additionally, each of the bulbous portions 1850 and 1865 have a taper, such as a Morse taper, that provides for a locked interference fit with tapered apertures 1835 and 1840 respectively.

Figure 19:
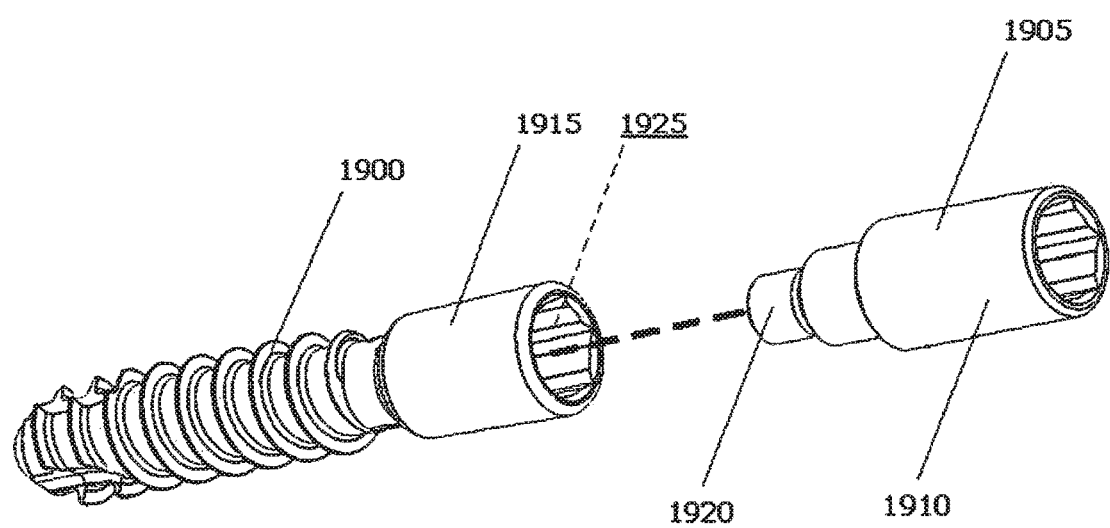
FIG. 19 is an exploded perspective view of a cover member for a lag screw according to an alternate embodiment of the invention.

In an alternate embodiment, as shown in FIG. 19, a lag screw member 1900 may include a cover or plug member 1905. The cover member 1905 includes a first end portion 1910 having substantially the same diameter as end portion 1915. The cover member 1905 also includes a second end portion 1920, which is smaller than the internal diameter of end portion 1915 and which is provided to be received inside aperture 1925 of lag screw member 1900.

It should be appreciated that any number of intramedullary fixation assemblies, such as intramedullary fixation assembly 800, may be inserted into the joints, for example, of the human foot in order to provide for compression of the bones of the foot. It should also be appreciated that the intramedullary fixation assembly 800 is delivered through an incision, thereby reducing the disruption to the plantar tissues while at the same time minimizing the tension on the skin. This allows for improved wound closure, reduced operating room time, reduction in the number of incisions required and reduction in the total length of incisions. It should also be appreciated that the intramedullary fixation assembly 800 may also be utilized to restore any of the other bones in the human body. It should also be appreciated that in other non-limiting embodiments, the intramedullary assembly 800 may be utilized with graft material (i.e., autograft, allograft or other biologic agent).

It should also be understood that this invention is not limited to the disclosed features and other similar method and system may be utilized without departing from the spirit and the scope of the invention.

While the invention has been described with reference to the preferred embodiment and alternative embodiments, which embodiments have been set forth in considerable detail for the purposes of making a complete disclosure of the invention, such embodiments are merely exemplary and are not intended to be limiting or represent an exhaustive enumeration of all aspects of the invention. The scope of the invention, therefore, shall be defined solely by the following claims. Further, it will be apparent to those of skill in the art that numerous changes may be made in such details without departing from the spirit and the principles of the invention. It should be appreciated that the invention is capable of being embodied in other forms without departing from its essential characteristics.

The invention claimed is:

1. An intramedullary fixation assembly for bone fusion, comprising:
   a first screw member extending along a first longitudinal axis, said first screw member having a first threaded portion at a first end and a bulbous portion comprising an exterior surface at a second end;
   a second screw member that couples to the first screw member, said second screw member extending along a second longitudinal axis from a first end to a second end, wherein the second screw member comprises a second threaded portion at the first end, a first aperture at a terminal end of the second end of the second screw member and a bore extending along a third axis from the first aperture to a second aperture on an exterior surface of the second screw member, wherein the second longitudinal axis and the third axis define an angle, and wherein the first aperture is offset from the second longitudinal axis at said angle; and wherein the first screw member couples to the second screw member by inserting the first end of the first screw member through the bore until the exterior surface of the bulbous portion of the first screw member abuts an interior surface of the bore.

2. The assembly of claim 1, wherein the bulbous portion resides entirely within the bore.

3. The assembly of claim 2, wherein the first threaded portion comprises a plurality of bone threads.

4. The assembly of claim 3, wherein the second threaded portion comprises a plurality of bone threads.

5. The assembly of claim 4, wherein the second threaded portion includes a self-tapping edge for removing bone material.

6. The assembly of claim 3, wherein the first threaded portion includes a self-tapping edge for removing bone material.

7. The assembly of claim 2, wherein the first screw member is cannulated.

8. The assembly of claim 2, wherein the bulbous portion comprises a spherical portion.

9. The assembly of claim 8, wherein the spherical portion is adapted to allow the first screw member to rotate within the bore to set an angle between the first screw member and the second screw member to at least one of a plurality of possible angles.

10. The assembly of claim 9, wherein the plurality of possible angles range from zero degrees to approximately 30 degrees.

11. The assembly of claim 1, wherein the bulbous portion resides at least partially within the bore, and further wherein the bulbous portion abuts the interior surface of the bore at the first aperture of the second screw member.

12. The assembly of claim 11, wherein the bulbous portion comprises a spherical portion.

13. The assembly of claim 12, wherein the spherical portion is adapted to allow the first screw member to rotate within the bore to set an angle between the first screw member and the second screw member to at least one of a plurality of possible angles.

14. The assembly of claim 13, wherein the plurality of possible angles range from zero degrees to approximately 30 degrees.

15. The assembly of claim 1, wherein the first threaded portion comprises a plurality of bone threads.

16. The assembly of claim 15, wherein the first threaded portion includes a self-tapping edge for removing bone material.

17. The assembly of claim 1, wherein the second threaded portion comprises a plurality of threads.

18. The assembly of claim 17, wherein the taper provides for an interference lock with the second screw member.

19. The assembly of claim 1, wherein the second threaded portion includes a self-tapping edge for removing bone material.

20. The assembly of claim 1, wherein the exterior surface of the bulbous portion includes a taper for providing an interference fit with the second screw member.

21. The assembly of claim 1, wherein the first screw member is cannulated.

* * * * *